United States Patent
Forbes et al.

(10) Patent No.: US 7,504,392 B2
(45) Date of Patent: Mar. 17, 2009

(54) 2,3,4,5-TETRAHYDRO-1H-3-BENZAZEPINES AND THEIR MEDICAL USE

(75) Inventors: Ian Thomson Forbes, Harlow (GB); Vincenzo Garzya, Harlow (GB); Andrew Derrick Gribble, Harlow (GB); Andrew Lightfoot, Harlow (GB); Andrew H. Payne, Harlow (GB); Graham Walker, Harlow (GB)

(73) Assignee: Glaxo Group Limited, Middlesex (GB)

( * ) Notice: Subject to any disclaimer, the term of this patent is extended or adjusted under 35 U.S.C. 154(b) by 572 days.

(21) Appl. No.: 10/515,998

(22) PCT Filed: May 28, 2003

(86) PCT No.: PCT/EP03/05727

§ 371 (c)(1),
(2), (4) Date: Jun. 9, 2005

(87) PCT Pub. No.: WO03/099786

PCT Pub. Date: Dec. 4, 2003

(65) Prior Publication Data

US 2005/0261279 A1    Nov. 24, 2005

(30) Foreign Application Priority Data

May 29, 2002  (GB) .................. 0212401.4
Dec. 23, 2002 (GB) .................. 0230053.1

(51) Int. Cl.
A61P 25/36   (2006.01)
A61K 31/4035 (2006.01)
A61K 31/4704 (2006.01)
A61K 31/55   (2006.01)
C07D 209/44  (2006.01)
C07D 217/02  (2006.01)
C07D 223/16  (2006.01)

(52) U.S. Cl. .................. 514/217.01; 540/594
(58) Field of Classification Search ............ 514/217.01; 540/594
See application file for complete search history.

(56) References Cited

U.S. PATENT DOCUMENTS 5,684,195 A   11/1997  Huang et al. .................. 564/90
6,200,978 B1  3/2001   Maw et al. .............. 514/254.05

FOREIGN PATENT DOCUMENTS

| DE | 10053799    | 5/2002  |
|----|-------------|---------|
| EP | 0285287 A   | 10/1988 |
| EP | 266949      | 11/1990 |
| EP | 431944      | 6/1991  |
| EP | 300725      | 6/1994  |
| WO | WO93/12796  | 12/1992 |
| WO | WO93/25534  | 12/1993 |
| WO | WO95/23150  | 2/1995  |
| WO | WO96/38471  | 5/1995  |
| WO | WO97/24405  | 12/1996 |
| WO | WO97/43262  | 5/1997  |
| WO | WO98/06699  | 8/1997  |
| WO | WO98/12180  | 9/1997  |
| WO | WO98/12192  | 9/1997  |
| WO | WO98/47869  | 4/1998  |
| WO | WO98/50363  | 4/1998  |
| WO | WO99/42462  | 2/1999  |
| WO | WO99/51571  | 4/1999  |
| WO | WO00/21959  | 10/1999 |
| WO | WO00/42036  | 1/2000  |
| WO | WO00/51975  | 3/2000  |
| WO | WO00/71510  | 5/2000  |
| WO | WO02/21951  | 9/2000  |
| WO | WO01/62737  | 2/2001  |
| WO | WO01/85695  | 5/2001  |
| WO | WO02/40471  | 5/2002  |
| WO | WO 02/40471 A | 5/2002 |
| WO | WO02/46164  | 6/2002  |
| WO | WO02/089811 | 11/2002 |
| WO | WO03/062205 | 12/2002 |
| WO | WO03/068732 | 2/2003  |
| WO | WO03/068751 | 2/2003  |
| WO | WO03/068752 | 2/2003  |
| WO | WO03/99792  | 5/2003  |
| WO | WO03/095428 | 11/2003 |
| WO | WO03/099786 | 12/2003 |

OTHER PUBLICATIONS

Grunewald, G.L. et al., "Synthesis, Biochemical Evaluation and Classical and Three-Demensional Quantitative Structure—Activity Relationship Studies of 7-Substituted 1, 2, 3, 4-tetrahydroisoquinolines and their Relative Affinities toward Phenylethanolamine N-Methyltransferase and the $\alpha_2$—Adrenoceptor," *J. Med. Chem* (1999) 42(1): 118-134.

Grunewald, G.L. et al., "Comparative Molecular Field Analysis (COMFA) Models of Phenylethanolamine N-Methyltransferase (PNMT) and the $\alpha_2$—Adrenoceptor: The Development of New, Highly Selective Inhibitors of PNMT" *Bioorganic & Medicinal Chemistry Letters* 9 (1999) 481-486.

*Primary Examiner*—Brenda L Coleman
(74) *Attorney, Agent, or Firm*—James M. Kanagy; Stephen Venetianer; Charles M. Kinzig

(57) ABSTRACT

The invention provides compounds of the formula

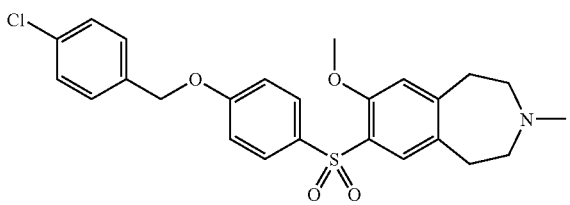

or a pharmaceutically acceptable salts thereof. The compounds are useful in therapy, in particular as antipsychotic agents.

7 Claims, No Drawings

2,3,4,5-TETRAHYDRO-1H-3-BENZAZEPINES AND THEIR MEDICAL USE

This application is a 371 National Phase entry of international application PCT/EP03/05727 filed May 28, 2003.

International patent application WO 01/62737 discloses amino pyrazole derivatives which are ligands for the neuropeptide Y subtype 5 receptor and are said to be useful in the treatment of disorders and disease associated with this receptor including, inter alia, obesity, anxiety, depression, pain and schizophrenia.

International patent application WO 01/85695 discloses tetrahydroisoquinoline analogues useful as growth hormone secretagogues. Such analogues are also said to be useful in the treatment of disorders including inter alia, obesity, schizophrenia, depression and Alzheimer's disease.

We have now found a novel group of phenylsulfonyl compounds which are useful particularly as antipsychotic agents.

According to the invention, there is provided a compound of formula (I):

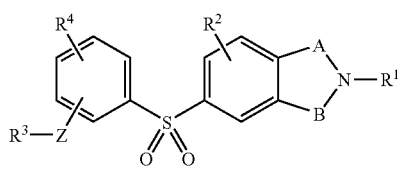

(I)

wherein

A and B represent the groups —$(CH_2)_m$— and —$(CH_2)_n$— respectively;

$R^1$ represents hydrogen or $C_{1-6}$alkyl;

$R^2$ represents hydrogen, halogen, hydroxy, cyano, nitro, hydroxy$C_{1-6}$alkyl, trifluoromethyl, trifluoromethoxy, $C_{1-6}$alkyl, $C_{1-6}$alkoxy, $C_{1-6}$fluoroalkoxy, —$(CH_2)_pC_{3-6}$cycloalkyl, —$(CH_2)_pOC_{3-6}$cycloalkyl, —$COC_{1-6}$alkyl, —$SO_2C_{1-6}$alkyl, —$SOC_{1-6}$alkyl, —S—$C_{1-16}$alkyl, —$CO_2C_{1-6}$alkyl, —$CO_2NR^5R^6$, —$SO_2NR^5R^6$, —$(CH_2)_pNR^5R^6$, —$(CH_2)_pNR^5COR^6$, optionally substituted aryl ring, optionally substituted heteroaryl ring or optionally substituted heterocyclyl ring;

$R^3$ represents optionally substituted aryl ring or optionally substituted heteroaryl ring;

$R^4$ represents hydrogen, hydroxy, $C_{1-6}$alkyl, $C_{1-6}$alkoxy, trifluoromethyl, trifluoromethoxy, halogen, —$OSO_2CF_3$, —$(CH_2)_pC_{3-6}$cycloalkyl, —$(CH_2)_qOC_{1-6}$alkyl or —$(CH_2)_p OC_{3-6}$cycloalkyl;

$R^5$ and $R^6$ each independently represent hydrogen, $C_{1-6}$alkyl or, together with the nitrogen or other atoms to which they are attached, form an azacycloalkyl ring or an oxo-substituted azacycloalkyl ring;

Z represents —$(CH_2)_rX$— wherein the —$(CH_2)_r$— group is attached to $R^3$, or —$X(CH_2)$, wherein X is attached to $R^3$, and wherein any of the —$CH_2$— groups may be optionally substituted by one or more $C_{1-6}$alkyl groups;

X represents oxygen, —$NR^7$ or $CH_2$— wherein the —$CH_2$ group may be optionally substituted by one or more $C_{1-6}$alkyl groups;

$R^7$ represents hydrogen or $C_{1-6}$alkyl;

m and n independently represent an integer selected from 1 and 2;

p independently represents an integer selected from 0, 1, 2 and 3;

q independently represents an integer selected from 1, 2 and 3;

r independently represents an integer selected from 0, 1, and 2;

or a pharmaceutically acceptable salt or solvate thereof.

It is to be understood that the present invention covers all combinations of particular and preferred groups described herein above.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "$C_{1-4}$fluoroalkoxy" refers to a straight or branched alkoxy group containing the specified number of carbon atoms wherein any of the carbon atoms may be substituted by one or more fluorine atoms.

As used herein, the term "cycloalkyl" refers to a non-aromatic hydrocarbon ring containing the specified number of carbon atoms. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{6-7}$cycloalkyl group is preferred.

As used herein, the term "halogen" refers to the elements fluorine, chlorine, bromine and iodine. Preferred halogens are fluorine, chlorine and bromine.

As used herein, the term "aryl" refers to a phenyl or a naphthyl ring.

As used herein, the term "heteroaryl" refers to a 5- or 6-membered heterocyclic aromatic ring or a fused bicyclic heteroaromatic ring system.

As used herein, the term "heterocyclyl" refers to a 3- to 7-membered monocyclic saturated ring containing at least one heteroatom independently selected from oxygen, nitrogen and sulfur. Examples of suitable heterocyclic rings include, but are not limited to, piperidine and morpholine.

As used herein, the term "5- or 6-membered heterocyclic aromatic ring" refers to a monocyclic unsaturated ring containing at least one heteroatom independently selected from oxygen, nitrogen and sulfur. Examples of suitable 5- and 6-membered heterocyclic aromatic rings include, but are not limited to, furyl, thienyl, pyrrolyl, oxazolyl, thiazolyl, imidazolyl, oxadiazolyl, thiadiazolyl, pyridyl, triazolyl, triazinyl, pyridazinyl, pyrazinyl, pyrimidinyl, pyrazolyl, isothiazolyl and isoxazolyl.

As used herein, the term "fused bicyclic heteroaromatic ring system" refers to a ring system comprising one six-membered unsaturated ring and one 5- or 6-membered unsaturated or saturated ring fused together, the ring system containing at least one heteroatom independently selected from oxygen, nitrogen and sulfur. Examples of suitable fused bicyclic heteroaromatic ring systems include, but are not limited to, indolyl, benzofuranyl, quinolyl and benzothienyl. Further examples include but are not limited to, isoquinolyl, quinolizinyl, naphthyridinyl, quinoxalinyl, quinazolinyl, cinnolinyl, isoindolyl, indolizinyl, indazolyl, pyrrolopyridinyl, benzimidazolyl, benzoxazolyl, benzisoxazolyl, benzothiazolyl, benzisothiazolyl, benzoxadiazolyl, benzothiadiazolyl, dihydrobenzothienyl, dihydrobenzofuranyl, benzodioxolanyl, methylenedioxyphenyl, dihydrobenzodioxinyl and the like.

As used herein, the term "azacycloalkyl ring" refers to a 4- to 7-membered monocyclic saturated ring containing one nitrogen atom. Examples of suitable azacycloalkyl rings are azetidine, pyrrolidine, piperidine and azepine.

As used herein, the term "oxo-substituted azacycloalkyl ring" refers to an azacycloalkyl ring as defined above substituted by one oxo group. Examples of suitable oxo-substituted azacycloalkyl rings include, but are not limited to, azetidinone, pyrrolidinone, piperidinone and azepinone.

When Z represents —$(CH_2)_rX$— wherein the —$(CH_2)_r$— group is attached to $R^3$, examples of Z include —O—, —$CH_2O$—, —$(CH_2)_2O$—, —$NR^7$—, —$CH_2NR^7$—, —$(CH_2)_2NR^7$—, —$CH_2$—, —$(CH_2)_2$—, —$(CH_2)_3$—, —NH—, —$CH_2NH$—, —$(CH_2)_2NH$, —$CH_2N(C_{1-6}alkyl)$ and —$(CH_2)_2N(C_{1-6}alkyl)$.

When Z represents —$X(CH_2)$, wherein X is attached to $R^3$, examples of Z include —O—, —$OCH_2$, —$O(CH_2)_2$, —$NR^7$—, —$NR^7CH_2$, —$NR^7(CH_2)_2$, —$CH_2$—, —$(CH_2)_2$, —$(CH_2)_3$—, —NH—, —$NHCH_2$—, —$NH(CH_2)_2$, —$N(C_{1-6}alkyl)$-, —$N(C_{1-6}alkyl)CH_2$— and —$N(C_{1-6}alkyl)(CH_2)_2$—.

As used herein, the term "substituted" refers to substitution with the named substituent or substituents, multiple degrees of substitution being allowed unless otherwise stated.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Most preferably the solvent used is water and the solvate may also be referred to as a hydrate.

It will be appreciated that for use in medicine the salts of formula (I) should be physiologically (i.e. pharmaceutically) acceptable. Suitable physiologically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, malic, mandelic, acetic, fumaric, glutamic, lactic, citric, tartaric, benzoic, benzenesulfonic, p-toluenesulfonic, methanesulfonic or naphthalenesulfonic acid. Other non-physiologically acceptable salts e.g. oxalates, may be used, for example in the isolation of compounds of formula (I) and are included within the scope of this invention. Also included within the scope of the invention are solvates and hydrates of the compounds of formula (I).

Certain of the compounds of formula (I) may form acid addition salts with one or more equivalents of the acid. The present invention includes within its scope all possible stoichiometric and non-stoichiometric forms thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The groups $R^2$, $R^3$-Z- and $R^4$ may be located on any position on their respective phenyl rings.

When $R^2$ represents optionally substituted aryl ring, optionally substituted heteroaryl ring or optionally substituted heterocyclyl ring, the optional substituents may be independently selected from $C_{1-6}$alkyl, $C_{1-6}$alkoxy, halogen, trifluoromethyl, trifluoromethoxy, cyano, —S—$C_{1-6}$alkyl, —$CONR^5R^6$ and —$NR^5COR^6$, wherein $R^5$ and $R^6$ have any of the meanings given hereinbefore.

When $R^3$ represents optionally substituted aryl ring or optionally substituted heteroaryl ring, the optional substituents may be independently selected from $C_{1-6}$alkyl, $C_{1-6}$alkoxy, halogen, trifluoromethyl, trifluoromethoxy, cyano, —S—$C_{1-6}$lalkyl, di($C_1$-alkyl)amino, $C_{1-6}$alkanoyl and $C_{1-4}$alkoxy$C_{1-4}$alkyl.

Preferably, $R^1$ represents hydrogen or $C_{1-4}$alkyl. More preferably, $R^1$ represents hydrogen, methyl, ethyl, n-propyl or isopropyl. Even more preferably, $R^1$ represents methyl.

Preferably, $R^2$ represents hydrogen, halogen, $C_{1-6}$alkyl, $C_{1-6}$alkoxy, $C_{1-6}$alkylthio or di$C_{1-6}$alkylamino. More preferably, $R^2$ represents hydrogen, halogen, $C_{1-4}$alkyl, $C_{1-4}$alkoxy or di$C_{1-6}$alkylamino. Even more preferably, $R^2$ represents methyl, methoxy, ethoxy, dimethylamino or isopropoxy.

Equally preferably, $R^2$ represents hydrogen, halogen, $C_{1-6}$alkyl or $C_{1-6}$alkoxy. More preferably, $R^2$ represents hydrogen, halogen, $C_{1-4}$alkyl or $C_{1-4}$alkoxy. Even more preferably, $R^2$ represents hydrogen, methoxy or bromo.

Preferably, when $R^2$ represents an optionally substituted aryl ring, an optionally substituted heteroaryl ring, or an optionally substituted heterocyclyl ring, the optional substituents are independently selected from chloro, fluoro, bromo, methyl, ethyl, t-butyl, methoxy, trifluoromethyl, trifluoromethoxy, cyano, —S-methyl, —$CONH_2$ and —NH-COMe.

Preferably, $R^3$ represents phenyl, pyridyl (e.g. 2-, 4- or 5-pyridyl), isoxazolyl (e.g. isoxazol-3-yl), thienyl (e.g. 2-thienyl), furyl (e.g. 2- or 3-furyl), thiazolyl (e.g. 2-thiazolyl), benzofuranyl (e.g. 1-benzofuranyl, 2-benzofuranyl or 5-(2,3-dihydrobenzofuranyl), benzothienyl (e.g. 2- or 3-benzothienyl), naphthyl (e.g. 2-naphthyl), benzodioxinyl (e.g. 2,3-dihydrobenzo[1,4]dioxin-6-yl or 2,3-dihydrobenzo[1,4]dioxin-2-yl) or benzodioxolanyl (e.g. 1,4-benzodioxolanyl) or methylenedioxyphenyl (e.g. 3,4-methylenedioxyphenyl), all of which may be optionally substituted. Most preferably, $R^3$ represents phenyl or optionally substituted phenyl.

Preferably, when $R^3$ represents optionally substituted phenyl, the optional substituents are independently selected from chloro (e.g. 4-chloro), fluoro (e.g. 4-fluoro), bromo, methyl, ethyl, t-butyl, methoxy, trifluoromethyl, trifluoromethoxy, cyano and —S-methyl. More preferably, the optional substituents are selected from chloro and fluoro.

Equally preferably when $R^3$ represents optionally substituted phenyl, the optional substituents are independently selected from chloro (e.g. 4-chloro, 2,4-, 3,4-, 2,6-dichloro), fluoro (e.g. 3- or 4-fluoro, 2,3-, 2,4- or 3,4-difluoro), methyl (e.g. 4-methyl), methoxy (e.g. 2-, 3- or 4-methoxy, 3,4-dimethoxy or 3,4,5-trimethoxy), bromo (e.g. 4-bromo), trifluoromethyl (e.g. 3- or 4-trifluoromethyl), i-propyl (e.g. 4-i-propyl), cyano (e.g. 5-cyano), dimethylamino (e.g. 3-dimethylamino), methoxymethylene (e.g. 4-methoxymethylene), acetyl (e.g. 4-acetyl) or any combination thereof (e.g. 2-chloro-4-fluoro).

Preferably when $R^3$ represents optionally substituted pyridyl, the optional substituent is methyl (e.g. 6-methyl).

Preferably when $R^3$ represents optionally substituted isoxazolyl, the optional substituent is methyl (e.g. 5-methyl).

Preferably when $R^3$ represents optionally substituted thienyl, the optional substituents are independently selected from methyl (e.g. 5-methyl) or chloro (e.g. 5-chloro).

Preferably when $R^3$ represents optionally substituted furyl, the optional substituents are independently selected from methyl (e.g. 5-methyl or 4,5-dimethyl), trifluoromethyl (e.g. 2-trifluoromethyl or ethyl (e.g. 2-ethyl).

Preferably when $R^3$ represents optionally substituted benzothienyl, the optional substituents are independently selected from methyl (e.g. 3-methyl) or chloro (e.g. 5-chloro).

When Z represents —$(CH_2)_rX$— or —$X(CH_2)_r$—, preferably X is —O— or —$NR^7$—. More preferably, X is —O— or —N(Me)—.

When Z represents —$CH_2)_rX$— or —$X(CH_2)_r$—, preferably r is 0 or 1.

When Z represents —$(CH_2)_rO$—, preferably r is 0 or 1.

More preferably, when Z represents —$(CH_2)_rX$— or —$X(CH_2)'X$— is —O— or —$NR^7$— and r is 0 or 1. Even more preferably, when Z is —$(CH_2)_rX$— or —$X(CH_2)_r$—, X is —O— or —N(Me)— and r is 0 or 1.

Preferably, Z represents —$CH_2O$—, —$OCH_2$—, —$NHCH_2$—, $CH_2NH$—, —O— or —N(Me)—. More preferably, Z represents —O— or —$CH_2O$—. Even more preferably, Z represents —$CH_2O$—.

Preferably, when r represents 0 or 1, $R^3$ represents phenyl or optionally substituted phenyl.

Preferably, when r represents 0 or 1 and $R^3$ represents phenyl or optionally substituted phenyl, the optional substituents on the phenyl ring are independently selected from chloro, fluoro, bromo, methoxy, trifluoromethyl, trifluoromethoxy and cyano.

Preferably, $R^4$ represents hydrogen, $C_{1-4}$alkyl or $C_{1-4}$alkoxy. More preferably, $R^4$ represents hydrogen, methyl or methoxy. Even more preferably, $R^4$ represents hydrogen.

Preferably, $R^5$ and $R^6$ independently represent hydrogen or $C_{1-4}$alkyl. More preferably, $R^5$ and $R^6$ independently represent hydrogen or methyl.

Preferably, $R^7$ represents hydrogen or $C_{1-4}$alkyl. More preferably, $R^7$ represents hydrogen.

Preferably, p represents 0.

In a first embodiment of the invention, the $R^2$ group is located at the para-position relative to the group B i.e. a compound of formula (IA)

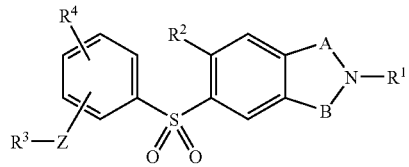

(IA)

or a pharmaceutically acceptable salt or solvate thereof wherein groups A, B, Z and $R^1$ to $R^4$ have any of the meanings as given hereinbefore.

When $R^2$ is located in the para-position i.e. compounds of formula (IA), $R^2$ is preferably hydrogen, methoxy, ethoxy, isopropoxy or dimethylamino.

In another embodiment of the invention, Z is located at the meta-position relative to the sulfone group i.e. a compound of formula (IB)

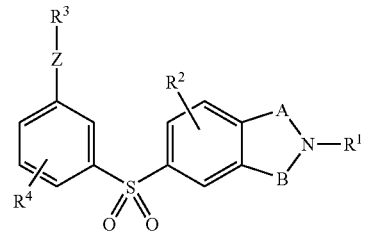

(IB)

or a pharmaceutically acceptable salt or solvate thereof wherein groups A, B, Z and $R^1$ to $R^4$ have any of the meanings as given hereinbefore.

When the $R^3$-Z- group is located in the meta-position i.e. compounds of formula (IB), and Z represents —$(CH_2)_rX$— or —$X(CH_2)_r$—, r is preferably 0 or 1 and $R^3$ is preferably phenyl or optionally substituted phenyl. When the $R^3$-Z group is located in the meta-position, and Z represents —$(CH_2)_r$X— or —$X(CH_2)_r$—, r is 0 or 1 and $R^3$ is phenyl or optionally substituted phenyl, the optional substituents on the phenyl ring are preferably independently selected from chloro or fluoro.

When $R^3$—$(CH_2)_rO$— is located in the meta-position and Z is —$(CH_2)_rO$—, r is preferably 0 or 1 and $R^3$ is preferably phenyl or optionally substituted phenyl. When $R^3$—$(CH_2)_rO$— is located in the meta-position, r is 0 or 1 and $R^3$ is phenyl or optionally substituted phenyl, the optional substituents on the phenyl ring are preferably independently selected from chloro or fluoro.

In another embodiment of the invention, the $R^3$-Z- group is located at the para-position relative to the sulfone group i.e. a compound of formula (IC)

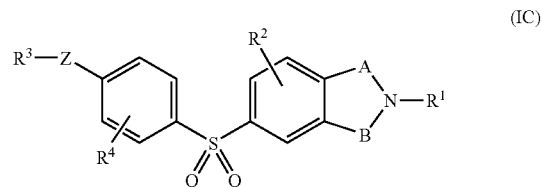

(IC)

or a pharmaceutically acceptable salt or solvate thereof wherein groups A, B, Z and $R^1$ to $R^4$ have any of the meanings as given hereinbefore.

When the $R^3$-Z- group is located in the para-position i.e. compounds of formula (IC), and Z represents —$CH_2)_rX$— or —$X(CH_2)_r$—, r is preferably 0 or 1 and $R^3$ is preferably phenyl or optionally substituted phenyl. When the $R^3$-Z- group is located in the para-position, and Z represents —$(CH_2)_rX$— or —$X(CH_2)_r$—, r is preferably 0 or 1 and $R^3$ is preferably phenyl or optionally substituted phenyl, the optional substituents on the phenyl ring are preferably chloro or fluoro.

When $R^3$—$(CH_2)_rO$— is located in the para-position and Z is —$(CH_2)_rO$—, r is preferably 0 or 1 and $R^3$ is preferably phenyl or optionally substituted phenyl. When $R^3$—$(CH_2)_rO$— is located in the meta-position, r is 0 or 1 and $R^3$ is phenyl or optionally substituted phenyl, the optional substituents on the phenyl ring are preferably independently selected from chloro or fluoro.

In another embodiment of the invention, the $R^3$-Z- group is located at the meta-position relative to the sulfone group and the $R^2$ group is located at the para-position relative to the group B i.e. a compound of formula (ID)

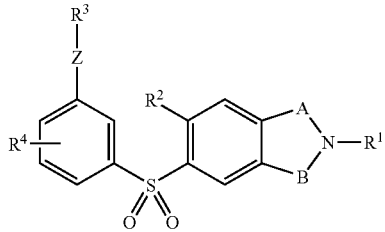

(ID)

or a pharmaceutically acceptable salt or solvate thereof wherein groups A, B, Z and $R^1$ to $R^4$ have any of the meanings as given hereinbefore.

In another embodiment of the invention, the $R^3$-Z- group is located at the para-position relative to the sulfone group and the $R^2$ group is located at the para-position relative to the group B i.e. a compound of formula (IE)

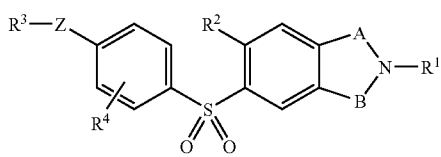

(IE)

or a pharmaceutically acceptable salt or solvate thereof wherein groups A, B, Z and $R^1$ to $R^4$ have any of the meanings as given hereinbefore.

In another embodiment of the invention, m is 1 and n is 1 and the invention is a compound of formula (IF):

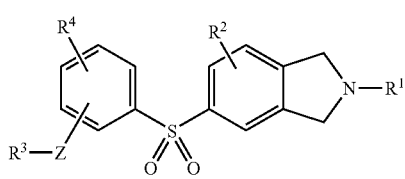

(IF)

or a pharmaceutically acceptable salt or solvate thereof wherein groups Z and $R^1$ to $R^4$ have any of the meanings as given hereinbefore.

In another embodiment of the invention, m is 2 and n is 1 and the invention is a compound of formula (IG):

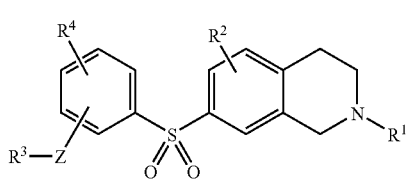

(IG)

or a pharmaceutically acceptable salt or solvate thereof wherein groups Z and $R^1$ to $R^4$ have any of the meanings as given hereinbefore.

In another embodiment of the invention, m is 1 and n is 2 and the invention is a compound of formula (IH):

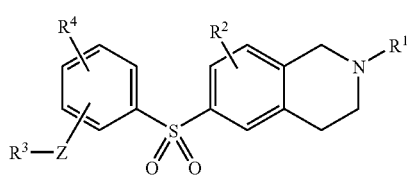

(IH)

or a pharmaceutically acceptable salt or solvate thereof wherein groups Z and $R^1$ to $R^4$ have any of the meanings as given hereinbefore.

In another embodiment of the invention, m is 2 and n is 2 and the invention is a compound of formula (IJ):

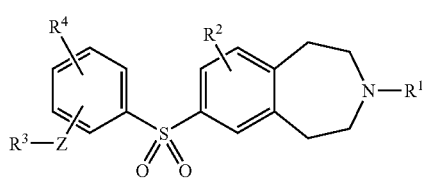

(IJ)

or a pharmaceutically acceptable salt or solvate thereof wherein groups Z and $R^1$ to $R^4$ have any of the meanings as given hereinbefore.

In another embodiment of the invention, m is 2 and n is 2, the $R^2$ group is located at the para-position relative to the group B, the $R^3$-Z- group is located at the meta-position relative to the sulfone group and the invention is a compound of formula (IK):

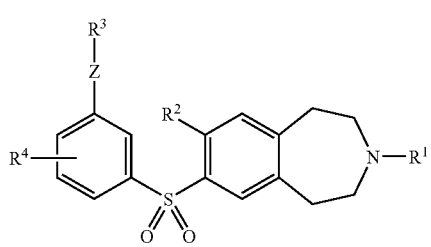

(IK)

or a pharmaceutically acceptable salt or solvate thereof wherein groups Z and $R^1$ to $R^4$ have any of the meanings as given hereinbefore.

In another embodiment of the invention, m is 2 and n is 2, the $R^2$ group is located at the para-position relative to the group B, the $R^3$-Z- group is located at the para-position relative to the sulfone group and the invention is a compound of formula (IL):

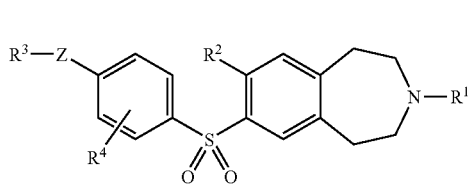

(IL)

or a pharmaceutically acceptable salt or solvate thereof wherein groups Z and $R^1$ to $R^4$ have any of the meanings as given hereinbefore.

In a preferred embodiment of the invention, for any of the compounds of the formulae (ID), (IE), (IF), (IG), (IH), (IJ), (IK), and (IL), Z is —(CH$_2$)$_r$O—.

In another embodiment of the invention, Z is —(CH$_2$)$_r$X— wherein X is oxygen and there is provided a compound of formula (IM):

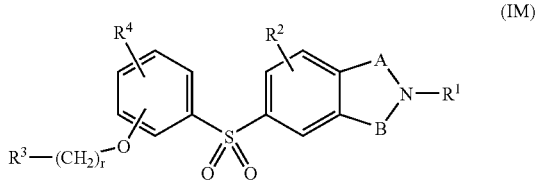

(IM)

wherein
A and B represent the groups —(CH$_2$)$_m$— and (CH$_2$)$_n$— respectively;
R$^1$ represents hydrogen or C$_{1-6}$alkyl;
R$^2$ represents hydrogen, halogen, hydroxy, cyano, nitro, hydroxyC$_{1-6}$alkyl, trifluoromethyl, trifluoromethoxy, C$_{1-6}$alkyl, C$_{1-6}$alkoxy, —(CH$_2$)$_p$C$_{3-6}$cycloalkyl, —(CH$_2$)$_p$OC$_{3-6}$cycloalkyl, —COC$_{1-6}$alkyl, —SO$_2$C$_{1-6}$alkyl, —SOC$_{1-6}$alkyl, —S—C$_{1-6}$alkyl, —CO$_2$C$_{1-6}$alkyl, —CO$_2$NR$^5$R$^6$, —SO$_2$NR$^5$R$^6$, —(CH$_2$)$_p$NR$^5$R$^6$, —(CH$_2$)$_p$NR$^5$COR$^6$, optionally substituted aryl ring, optionally substituted heteroaryl ring or optionally substituted heterocyclyl ring;
R$^3$ represents optionally substituted aryl ring or optionally substituted heteroaryl ring;
R$^4$ represents hydrogen, hydroxy, C$_{1-6}$alkyl, C$_{1-6}$alkoxy, trifluoromethyl, trifluoromethoxy, halogen, —OSO$_2$CF$_3$, —(CH$_2$)$_p$C$_{3-6}$cycloalkyl, —(CH$_2$)$_q$OC$_{1-6}$alkyl or —(CH$_2$)$_p$OC$_{3-6}$cycloalkyl;
R$^5$ and R$^6$ each independently represent hydrogen, C$_{1-6}$alkyl or, together with the nitrogen or other atoms to which they are attached, form an azacycloalkyl ring or an oxo-substituted azacycloalkyl ring;
m and n independently represent an integer selected from 1 and 2;
p independently represents an integer selected from 0, 1, 2 and 3;
q independently represents an integer selected from 1, 2 and 3;
r independently represents an integer selected from 0, 1, and 2;

or a pharmaceutically acceptable salt or solvate thereof.

In another embodiment of the invention, the R$^2$ group is located at the meta-position relative to the group B and the invention is a compound of formula (IN):

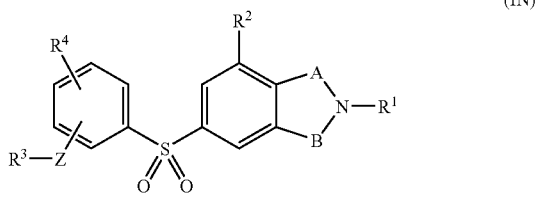

(IN)

wherein groups Z, A, B and R$^1$ to R$^4$ have any of the meanings as given hereinbefore.

In another embodiment of the invention, there is provided a compound of formula (IP):

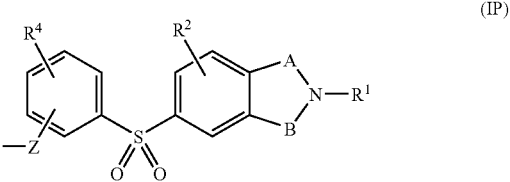

(IP)

wherein
A and B represent the groups —(CH$_2$)$_m$— and —CH$_2$)$_n$— respectively;
R$^1$ represents hydrogen or C$_{1-6}$alkyl;
R$^2$ represents hydrogen, halogen, hydroxy, cyano, nitro, hydroxyC$_{1-6}$alkyl, trifluoromethyl, trifluoromethoxy, C$_{1-6}$alkyl, C$_{1-6}$alkoxy, —(CH$_2$)$_p$C$_{3-6}$cycloalkyl, —(CH$_2$)$_p$OC$_{3-6}$cycloalkyl, —COC$_{1-6}$alkyl, —SO$_2$C$_{1-6}$alkyl, —SOC$_{1-6}$alkyl, —S—C$_{1-6}$alkyl, —CO$_2$C$_{1-6}$alkyl, —CO$_2$NR$^5$R$^6$, —SO$_2$NR$^5$R$^6$, —(CH$_2$)$_p$NR$^5$R$^6$, —(CH$_2$)$_p$NR$^5$COR$^6$, optionally substituted aryl ring, optionally substituted heteroaryl ring or optionally substituted heterocyclyl ring;
R$^3$ represents optionally substituted aryl ring or optionally substituted heteroaryl ring;
R$^4$ represents hydrogen, hydroxy, C$_{1-6}$alkyl, C$_{1-6}$-alkoxy, trifluoromethyl, trifluoromethoxy, halogen, —OSO$_2$CF$_3$, —(CH$_2$)$_p$C$_{3-6}$cycloalkyl, —(CH$_2$)$_q$OC$_{1-6}$alkyl or —(CH$_2$)$_p$ OC$_{3-6}$cycloalkyl;
R$^5$ and R$^6$ each independently represent hydrogen, C$_1$-alkyl or, together with the nitrogen or other atoms to which they are attached, form an azacycloalkyl ring or an oxo-substituted azacycloalkyl ring;
Z represents —(CH$_2$)$_r$X— wherein the —(CH$_2$)— group is attached to R$^3$, or ——X(CH$_2$)$_r$—, wherein X is attached to R$^3$, and wherein any of the —CH$_2$— groups may be optionally substituted by one or more C$_{1-6}$alkyl groups;
X represents oxygen, —NR$^7$ or —CH$_2$— wherein the —CH$_2$— group may be optionally substituted by one or more C$_{1-6}$alkyl groups;
R$^7$ represents hydrogen or C$_{1-6}$alkyl;
m and n independently represent an integer selected from 1 and 2;
p independently represents an integer selected from 0, 1, 2 and 3;
q independently represents an integer selected from 1, 2 and 3;
r independently represents an integer selected from 0, 1, and 2;

or a pharmaceutically acceptable salt or solvate thereof.

Particular compounds according to the invention include those incorporated in Tables 1 to 7 and those specifically exemplified and named hereinafter including, without limitation:—

7-Methoxy-8-(3-phenoxy-benzenesulfonyl)-2,3,4,5-tetrahydro-1H-3-benzazepine;
7-Methoxy-3-methyl-8-(3-phenoxy-benzenesulfonyl)-2,3,4,5-tetrahydro-1H-3-benzazepine;
7-(3-Benzyloxyphenylsulfonyl)-2,3,4,5-tetrahydro-3-benzazepine;
7-[4-(4-Chloro-benzyloxy)-benzenesulfonyl]-8-methoxy-3-methyl-2,3,4,5-tetrahydro-1H-3-benzazepine;

(4-Fluoro-benzyl)-[4-(8-methoxy-3-methyl-2,3,4,5-tetrahydro-1H-3-benzazepine-7-sulfonyl)-phenyl]-amine;
[4-(8-Methoxy-3-methyl-2,3,4,5-tetrahydro-1H-3-benzazepine-7-sulfonyl)-phenyl]-phenyl-amine;
7-[4-(4-Chloro-phenoxymethyl)-benzenesulfonyl]-B-methoxy-3-methyl-2,3,4,5-tetrahydro-1H-3-benzazepine;
4-Chloro-phenyl)-[4-(8-methoxy-3-methyl-2,3,4,5-tetrahydro-1H-3-benzazepine-7-sulfonyl)-benzyl]-amine;
7-[4-(4-Fluorobenzyl)benzenesulfonyl]-8-methoxy-3-methyl-2,3,4,5-tetrahydro-1H-3-benzazepine;
7-[4-(3-Fluoro-benzyloxy)-benzenesulfonyl]-6-methoxy-1,2,3,4-tetrahydro-isoquinoline, and
5-Methoxy-2-methyl-6-[4-(3-trifluoromethyl-benzyloxy)-benzenesulfonyl]-2,3-dihydro-1H-isoindole;
(2-Methoxy-benzyl)-[4-(8-methoxy-3-methyl-2,3,4,5-tetrahydro-1H-3-benzazepine-7-sulfonyl)-phenyl]-amine;
7-[4-(4-Chloro-phenoxymethyl)-benzenesulfonyl]-8-ethoxy-3-methyl-2,3,4,5-tetrahydro-1H-3-benzazepine;
[4-(8-Ethoxy-3-methyl-2,3,4,5-tetrahydro-1H-3-benzazepine-7-sulfonyl)-benzyl]-(2-methoxy-phenyl)-amine;
{8-[4-(4-Fluoro-phenoxymethyl)-benzenesulfonyl]-3-methyl-2,3,4,5-tetrahydro-1H-3-benzazepin-7-yl}-dimethyl-amine;
6-Ethoxy-7-[4-(4-fluoro-benzyloxy)-benzenesulfonyl]-1,2,3,4-tetrahydro-isoquinoline hydrochloride;
(3-Methoxy-benzyl)-[4-(6-methoxy-1,2,3,4-tetrahydro-isoquinoline-7-sulfonyl)-phenyl]-methyl-amine hydrochloride;
7-[4-(4-Chlorophenoxymethyl)benzenesulfonyl]-6-methoxy-1,2,3,4-tetrahydroisoquinoline hydrochloride salt; and
3-Methyl-7-{(4-(2-methoxybenzyloxy)-phenylsulfonyl}-9-phenyl-1,2,4,5-tetrahydro-3-benzazepine.

The compounds of the present invention may be in the form of their free base or physiologically acceptable salts thereof, particularly the monohydrochloride or monomesylate salts or pharmaceutically acceptable derivatives thereof.

The present invention also provides a general process (A) for preparing compounds of formula (I) which process comprises:

reacting a compound of formula (II)

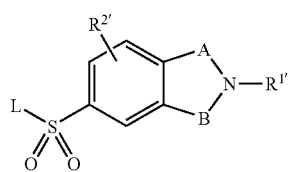

with a compound of formula (III)

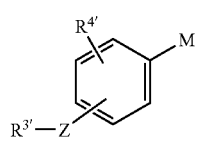

wherein L is a leaving group, such as fluoro, chloro, alkoxy or aryloxy, M is a metal, such as lithium or magnesium, and $R^{1'}$-$R^{4'}$ represent $R^1$ to $R^4$ as hereinbefore defined or are groups that may be readily convertible to $R^1$ to $R^4$, and Z, A and B are as hereinbefore defined.

This general method (A) can be conveniently performed by mixing the two components at preferably −70° C. to room temperature in a suitable solvent such as tetrahydrofuran or ether for 10 minutes to 18 hours. Removal of certain $R^{1'}$ protecting groups e.g. trifluoroacetyl, can also take place simultaneously during this process.

The present invention also provides a general process (B) for preparing compounds of formula (I), which process comprises:

reacting a compound of formula (IV)

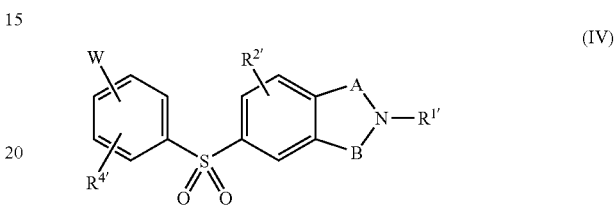

with a compound of formula (V)

wherein W is OH or $NHR^7$, and Y is a leaving group, such as bromo, iodo, chloro, fluoro, hydroxy, mesylate or triflate;
or Y is OH, $NHR^7$, CHO, MgBr or ZnCl and W is a leaving group, such as fluoro, chloro, bromo or triflate and r, A, B and $R^7$ are as hereinbefore defined and $R^{1'}$-$R^{4'}$ represent $R^1$ to $R^4$ as hereinbefore defined or are groups that may be readily convertible to $R^1$ to $R^4$.

Examples of general process (B) include:
a) W is OH, Y is Br and r is 1 which can be conveniently performed by heating the two reactants in an inert solvent e.g. dimethylformamide or dimethylsulfoxide, under basic conditions e.g. potassium carbonate or sodium hydride, optionally at elevated temperature e.g. 100° C.
b) W is OH, Y is OH and r is 1 which can be conveniently carried out using Mitsunobu conditions in the presence of triphenylphosphine and diisopropyl azodicarboxylate in tetrahydrofuran at room temperature.
c) W is $NHR^7$, Y is CHO and r is 0 which can be conveniently carried out using reductive alkylation conditions e.g. sodium triacetoxyborohydride in dichloroethane at room temperature.
d) W is F, Y is OH and r is 1 which can be conveniently carried out under basic conditions e.g. in the presence of sodium hydride in dimethylsulfoxide, optionally at elevated temperature.
e) W is F, Y is OH and r is 0 which can be conveniently carried out under basic conditions e.g. in the presence of sodium hydride in dimethylsulfoxide, optionally at elevated temperature.
f) W is F, Y is $NHR^7$ and r is 1 which can be conveniently carried out by heating the reactants in an inert solvent e.g. dimethylsulfoxide at elevated temperature.
g) W is F, Y is $NHR^7$ and r is 0 which can be conveniently carried out under basic conditions e.g. in the presence of sodium hydride or lithium hexamethyldisilazide in an inert solvent, at room temperature.
h) W is Br, Y is ZnCl and r is 1 which can be conveniently out in an inert solvent e.g. tetrahydrofuran in the presence palladium tetrakis(triphenylphosphine) optionally at elevated temperature e.g. 60° C.

i) W is NHR$^7$, Y is Br and r is 0 which can be conveniently carried out in an inert solvent using palladium catalysed conditions as published by Buchwald (J. Org. Chem. 1997, 1264).

j) W is OTf, Y is NHR$^7$ and r is 0 which can be conveniently carried out in an inert solvent using palladium catalysed conditions as published by Buchwald (J. Org. Chem. 1997, 1264).

k) W is NHR$^7$, Y is Br and r is 1 which can be conveniently performed by heating the 2 reactants in an inert solvent e.g. dimethylformamide or dimethylsulfoxide, under basic conditions e.g. potassium carbonate or sodium hydride, optionally at elevated temperature e.g. 100° C.

The present invention also provides a general process (C) for preparing compounds of formula (I), which process comprises:

reacting a compound of formula (VI)

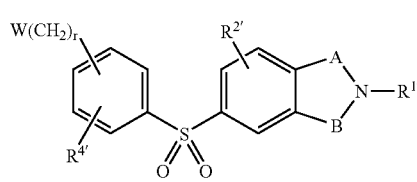

(VI)

with a compound of formula (VII)

R$^{3'}$—Y     (VII)

wherein W is OH, NHR$^7$ or CHO and Y is a leaving group, such as bromo, iodo, chloro, fluoro, hydroxy, mesylate or triflate, or Y is OH or NHR$^7$ and r, A, B and R$^7$ are as hereinbefore defined and R$^1$-R$^4$ represent R$^1$ to R$^4$ as hereinbefore defined or are groups that may be readily convertible to R$^1$ to R$^4$.

Examples of general process (C) include:

a) W is OH, r is 1 and Y is OH which can be conveniently carried out using Mitsunobu conditions in the presence of triphenylphosphine and diisopropyl azodicarboxylate in tetrahydrofuran at room temperature.

b) W is OH, r is 1 and Y is F which can be conveniently carried out using standard aromatic nucleophilic substitution conditions e.g. in an inert solvent in the presence of base such as sodium hydride c) W is CHO, r is 0 and Y is NHR$^7$ which can be conveniently carried out using reductive alkylation conditions e.g. sodium triacetoxyborohydride in dichloroethane at room temperature d) W is Br, r is 1 and Y is OH which can be conveniently performed by heating the two reactants in an inert solvent e.g. dimethylformamide or dimethylsulfoxide, under basic conditions e.g. potassium carbonate or sodium hydride, optionally at elevated temperature e.g. 100° C.

e) W is Br, r is 1 and Y is NHR$^7$ which can be conveniently performed by heating the two reactants in an inert solvent e.g. dimethylformamide or dimethylsulfoxide, under basic conditions e.g. potassium carbonate or sodium hydride, optionally at elevated temperature e.g. 100° C.

The present invention also provides a general process (D) for preparing compounds of formula (I) which process comprises:

reacting a compound of formula (VIII)

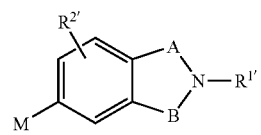

(VIII)

with a compound of formula (IX)

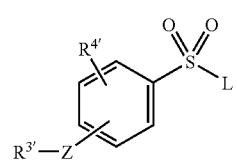

(IX)

wherein L is a leaving group, such as fluoro, chloro, alkoxy or aryloxy, M is a metal, such as lithium or magnesium, or M is hydrogen, Z, A and B are as hereinbefore defined and R$^{1'}$-R$^{4'}$ represent R$^1$ to R$^4$ as hereinbefore defined or are groups that may be readily convertible to R$^1$ to R$^4$. This general method (D) can be conveniently performed by mixing the two components at preferably −70° C. to room temperature in a suitable solvent such as tetrahydrofuran or ether for 10 minutes to 18 hours. Alternatively, where M is H, this general method can be conveniently performed by treating (VIII) and (IX) with a Lewis acid under Friedel-Crafts conditions at elevated temperature in a suitable solvent.

The present invention also provides a general process (E) for preparing compounds of formula (I) which process comprises:

reacting a compound of formula (X)

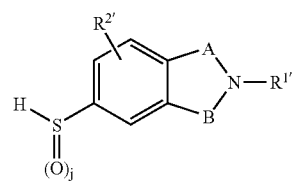

(X)

with a compound of formula (XI)

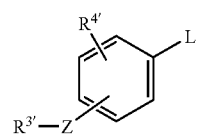

(XI)

wherein L is a leaving group, such as halogen (e.g. fluoro or bromo or iodo) or triflate, j is 0, 1 or 2, and Z, A and B are as hereinbefore defined and R$^{1'}$-R$^{4'}$ represent R$^1$ to R$^4$ as hereinbefore defined or are groups that may be readily convertible to R$^1$ to R$^4$. This general method (E) can be conveniently performed by mixing the two components in a suitable solvent such as dimethylformamide, in the presence of base e.g. sodium hydride, in the presence of copper iodide at elevated temperature e.g. 120° C. or palladium catalysed cross coupling as described in Tetrahedron 2001, 3069, and where necessary oxidising, the intermediate sulfide or sulfoxide.

The present invention also provides a general process (F) for preparing compounds of formula (I) which process comprises:

reacting a compound of formula (XII)

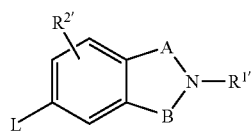

(XII)

with a compound of formula (XIII)

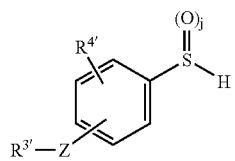

(XIII)

wherein L is a leaving group, such as halogen e.g. (bromo or iodo) or triflate, j is 0, 1 or 2, and Z, A and B are as hereinbefore defined and $R^{1'}$-$R^{4'}$ represent $R^1$ to $R^4$ as hereinbefore defined or are groups that may be readily convertible to $R^1$ to $R^4$. This general method (F) can be conveniently performed by palladium catalysed cross coupling as described in Tetrahedron 2001, 3069, and where necessary oxidising, the intermediate sulfide or sulfoxide.

Interconversion of one of the $R^{1'}$ to $R^{5'}$ groups to the corresponding $R^1$ to $R^4$ groups typically arises when one compound of formula (I) is used as the immediate precursor of another compound of formula (I), or when it is easier to introduce a more complex or reactive substituent at the end of a synthetic sequence.

For example, conversion of $R^{1'}$ from a t-butoxycarbonyl (BOC) group to hydrogen is conducted by the treatment of the N-BOC protected compound with hydrogen chloride in ethanol or dioxan at room temperature.

Conversion of $R^{1'}$ from hydrogen to an alkyl group is conducted by the treatment of the NH compound with the appropriate aldehyde in dichloroethane in the presence of a reducing agent, such as sodium triacetoxyborohydride, or by the treatment of the NH compound with the appropriate alkyl halide, such as iodomethane, under standard alkylation conditions (potassium carbonate in DMF at 60° C.).

Compounds of formula (II) are known in the literature or may be prepared by known processes, for example, chlorosulfonation of the aromatic ring using chlorosulfonic acid. Conversion to the sulfonyl fluoride can be achieved, if required, by reaction with potassium fluoride in acetonitrile at room temperature. Suitable examples of an $R^{1'}$ protecting group are trifluoroacetyl or the t-butoxycarbonyl (BOC) group.

Compounds of formula (III) are commercially available or may be prepared by established procedures, for example lithiation of the corresponding bromobenzene in tetrahydrofuran at low temperature, with for example t-butyl lithium or formation of the Grignard reagent from the appropriate bromobenzene.

Compounds of formula (IV) may be prepared using a similar process to general process A, using a suitably functionalised Grignard or organolithium reagent, where necessary utilising protection or interconversion of the functional group W. For example, compounds of formula (IV) in which W is 4-$NH_2$ can be prepared from the corresponding 4-fluoro analogue by displacement with the anion of trifluoroacetamide followed by hydrolysis, or alternatively by hydrolysis of a protected amine function e.g. bis(trimethylsilyl)N. Compounds of formula (IV) in which W is OH can be prepared by hydrolysis of the corresponding t-butyldimethylsilyl ether.

Compounds of formula (V) are commercially available or readily prepared from commercially available starting materials.

Compounds of formula (VI) may be prepared using a similar process to general process A, using a suitably functionalised Grignard or organolithium reagent, where necessary utilising protection or interconversion of the functional group W. For example, compounds of formula (VI) in which W is CHO and r is 0 can be prepared by hydrolysis of the corresponding diethyl acetal. Compounds of formula (VI) in which r is 1 and W is OH can be prepared by $NaBH_4$ reduction of the corresponding aldehyde. Compounds of formula (VI) in which r is 1 and W is Br can be prepared from the corresponding alcohol by treatment with $CBr_4$ and triphenylphosphine.

Compounds of formula (VII) are commercially available or readily prepared from commercially available starting materials.

Compounds of formula (VII) can be prepared by halogenation (e.g. iodination or bromination) of compounds of formula (VII) where M is H, followed by formation of the lithium or Grignard reagent.

Compounds of formula (IX) may be prepared by chlorosulfonylation of the aromatic ring, or by oxidation of the corresponding thiol or disulfide. Conversion to the sulfonyl fluoride can be achieved, if required, by reaction with potassium fluoride in acetonitrile at room temperature.

Compounds of formula (X) may be prepared by reduction of compounds of formula (II) using for example lithium aluminium hydride in tetrahydrofuran to give the thiol, or using sodium bisulphite and sodium bicarbonate in tetrahydrofuran/water to give the sulfinic acid.

Compounds of formula (XI) are commercially available or readily prepared from commercially available starting materials.

Compounds of formula (XII) can be prepared by halogenation (e.g. iodination or bromination) of compounds of formula (XII) where L is H, or conversion of L is OH to triflate using standard methodology.

Compounds of formula (XIII) may be prepared by reduction of compounds of formula (IX) using for example lithium aluminium hydride in tetrahydrofuran to give the thiol, or using sodium bisulphite and sodium bicarbonate in tetrahydrofuran/water to give the sulfinic acid.

Compounds of formula (I) have antagonist affinity for the serotonin 5-$HT_{2C}$, 5-$HT_{2A}$ and 5-$HT_6$ receptors. These properties may give rise to anti-psychotic activity (e.g. improved effects on cognitive dysfunction) activity with reduced extrapyramidal side effects (eps), and/or anxiolytic/antidepressant activity. These could include, but are not limited to, attenuation of cognitive symptoms via 5-$HT_6$ receptor blockade (see Reavill, C. and Rogers, D. C., 2001, Investigational Drugs 2, 104-109), and reduced anxiety (see for example Kennett et al., Neuropharmacology 1997 April-May; 36 (4-5): 609-20), protection against EPS (Reavill et al., Brit. J.

Pharmacol., 1999; 126: 572-574) and antidepressant activity (Bristow et al., Neuropharmacology 39:2000; 1222-1236) via $5-HT_{2C}$ receptor blockade.

Certain compounds of formula (I) have also been found to exhibit affinity for dopamine receptors, in particular the $D_3$ and $D_2$ receptors, and are useful in the treatment of disease states which require modulation of such receptors, such as psychotic conditions. Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable eps associated with many neuroleptic agents. Without wishing to be bound by theory, it has been suggested that blockade of the dopamine $D_3$ receptor may give rise to beneficial antipsychotic activity without significant eps (see for example Sokoloff et al, Nature, 1990; 347: 146-151; and Schwartz et al, Clinical Neuropharmacology, Vol 16, No. 4, 295-314, 1993).

Compounds of formula (I) may also exhibit affinity for other receptors not mentioned above, resulting in beneficial antipyschotic activity.

The compounds of formula (I) are of use as antipsychotic agents for example in the treatment of schizophrenia, schizoaffective disorders, schizophreniform diseases, psychotic depression, mania, acute mania, paranoid and delusional disorders. Furthermore, they may have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety; agitation; tension; social or emotional withdrawal in psychotic patients; cognitive impairment including memory disorders such as Alzheimer's disease; psychotic states associated with neurodegenerative disorders, e.g. Alzheimer's disease; eating disorders; obesity; sexual dysfunction; sleep disorders; emesis; movement disorders; obsessive-compulsive disorders; amnesia; aggression; autism; vertigo; dementia; circadian rhythm disorders; convulsions; epilepsy; and gastric motility disorders e.g. IBS.

Therefore, the invention provides a compound of formula (I) as hereinbefore described or a pharmaceutically acceptable salt or solvate thereof for use in therapy.

The invention also provides a compound of formula (I) or a pharmaceutically acceptable salt or solvate thereof for use in the treatment of a condition which requires modulation of a dopamine receptor.

The invention also provides a compound of formula (I) as hereinbefore described or a pharmaceutically acceptable salt or solvate thereof for use in the treatment of psychotic disorders, schizophrenia, Parkinsons disease, substance abuse, dyskinetic disorders, depression, bipolar disorder, anxiety, cognitive impairment, eating disorders, obesity, sexual dysfunction, sleep disorders, emesis, movement disorders, obsessive-compulsive disorders, amnesia, aggression, autism, vertigo, dementia, circadian rhythm disorders and gastric motility disorders.

The invention also provides the use of a compound of formula (I) as hereinbefore described or a pharmaceutically acceptable salt or solvate thereof in the manufacture of a medicament for the treatment of a condition which requires modulation of a dopamine receptor.

The invention also provides the use of a compound of formula (I) as hereinbefore described or a pharmaceutically acceptable salt or solvate thereof in the manufacture of a medicament for the treatment of psychotic disorders, schizophrenia, Parkinsons disease, substance abuse, dyskinetic disorders, depression, bipolar disorder, anxiety, cognitive impairment, eating disorders, obesity, sexual dysfunction, sleep disorders, emesis, movement disorders, obsessive-compulsive disorders, amnesia, aggression, autism, vertigo, dementia, circadian rhythm disorders and gastric motility disorders.

The invention also provides a method of treating a condition which requires modulation of a dopamine receptor, which comprises administering to a mammal in need thereof an effective amount of a compound of formula (I) as hereinbefore described or a pharmaceutically acceptable salt or solvate thereof.

The invention also provides a method of treating psychotic disorders, schizophrenia, Parkinsons disease, substance abuse, dyskinetic disorders, depression, bipolar disorder, anxiety, cognitive impairment, eating disorders, obesity, sexual dysfunction, sleep disorders, emesis, movement disorders, obsessive-compulsive disorders, amnesia, aggression, autism, vertigo, dementia, circadian rhythm disorders and gastric motility disorders which comprises administering to a mammal in need thereof an effective amount of a compound of formula (I) as hereinbefore described or a pharmaceutically acceptable salt or solvate thereof.

A preferred use for dopamine antagonists according to the present invention is in the treatment of psychotic disorders, schizophrenia, Parkinsons disease, substance abuse, dyskinetic disorders, depression, bipolar disorder, anxiety and cognitive impairment.

"Treatment" includes prophylaxis, where this is appropriate for the relevant condition(s).

It will be appreciated by those skilled in the art that the compounds according to the invention may advantageously be used in conjunction with one or more other therapeutic agents, for instance, different antidepressant agents such as $5HT_3$ antagonists, serotonin agonists, NK-1 antagonists, selective serotonin reuptake inhibitors (SSRI), noradrenaline re-uptake inhibitors (SNRI), tricyclic antidepressants, dopaminergic antidepressants, $H_3$ antagonists, $5HT_{1A}$ antagonists, $5HT_{1B}$ antagonists, $5HT_{1D}$ antagonists, $D_1$ agonists, $M_1$ agonists and/or anticonvulsant agents.

Suitable $5HT_3$ antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the inventions include for example divalproex, carbamazepine and diazepam.

It will be appreciated that the compounds of the combination or composition may be administered simultaneously (either in the same or different pharmaceutical formulations), separately or sequentially.

For use in medicine, the compounds of the present invention are usually administered as a standard pharmaceutical composition. The present invention therefore provides in a further aspect a pharmaceutical composition comprising a compound of formula (I) as hereinbefore described or a pharmaceutically (i.e. physiologically) acceptable salt thereof and a pharmaceutically (i.e. physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) as hereinbefore described and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

No toxicological effects are indicated/expected when a compound of the invention is administered in the above mentioned dosage range.

Biological Test Methods

Binding Experiments on Cloned Dopamine (e.g. D2 and D3) Receptors

The ability of the compounds to bind selectively to human D2/D3 dopamine receptors can be demonstrated by measuring their binding to cloned receptors. The inhibition constants ($K_i$) of test compounds for displacement of [$^{125}$I]-Iodosulpride binding to human D2/D3 receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −80° C. Crude cell membranes were prepared by homogenisation followed by high-speed centrifugation, and characterisation of cloned receptors achieved by radioligand binding.

Preparation of CHO cell membranes: Cell pellets were gently thawed at room temperature, and resuspended in about 20 volumes of ice-cold Extraction buffer; 5 mM EDTA, 50 mM Trizma pre-set crystals (pH7.4@37° C.), 1 mM $MgCl_2$, 5 mM KCl and 120 mM NaCl. The suspension was homogenised using an Ultra-Turrax at full speed for 15 seconds. The homogenate was centrifuged at 18,000 r.p.m for 15 min at 4° C. in a Sorvall RC5C centrifuge. Supernatant was discarded, and homogenate re-suspended in extraction buffer then centrifugation was repeated. The final pellet was resuspended in 50 mM Trizma pre-set crystals (pH 7.4 @ 37° C.) and stored in 1 ml aliquot tubes at −80° C. (D2=3.0 E+08 cells, D3=7.0 E+07 cells and D4=1.0 E+08 cells). The protein content was determined using a BCA protocol and bovine serum albumin as a standard (Smith, P. K., et al., Measurement of protein using bicinchoninic acid. Anal. Biochem. 150, 76-85 (1985)).

Binding experiments: Crude D2/D3 cell membranes were incubated with 0.03 nM [$^{125}$I]-Iodosulpride (~2000 Ci/mmol; Amersham, U. K., and the test compound in a buffer containing 50 mM Trizma pre-set crystals (pH 7.4 @ 37° C.), 120 mM NaCl, 5 mM KCl, 2 mM $CaCl_2$, 1 mM $MgCl_2$, 0.3% (w/v) bovine serum albumin. The total volume is 0.2 ml and incubated in a water bath at 37° C. for 40 minutes. Following incubation, samples were filtered onto GF/B Unifilters using a Can berra Packard Filtermate, and washed four times with ice-cold 50 mM Trizma pre-set crystals (pH 7.4 @ 37° C.). The radioactivity on the filters was measured using a Can berra Packard Topcount Scintillation counter. Non-specific binding was defined with 10 μM SKF-102161 (YM-09151). For competition curves, 10 serial log concentrations of competing cold drug were used (Dilution range: 10 μM-10 pM). Competition curves were analysed using Inflexion, an iterative curve fitting programme in Excel. Results were expressed as pKi values where $pK_i = -\log 10[K_i]$.

The exemplified compounds have $pK_i$ values within the range of 6.3-8.9 at the dopamine $D_3$ receptor.

The exemplified compounds have $pK_i$ values within the range of 5.6-8.5 at the dopamine $D_2$ receptor.

Binding Experiments on Cloned 5-HT$_6$ Receptors

Compounds can be tested following the procedures outlined in WO 98/27081.

The exemplified compounds have $pK_i$ values within the range of 7.2-10.0 at the serotonin 5-HT$_6$ receptor.

Binding Experiments on Cloned 5-HT$_{2A}$ and 5-HT$_{2C}$ Receptors

Compounds can be tested following the procedures outlined in WO 94/04533.

The exemplified compounds have $pK_i$ values within the range of 7.0-9.9 at the serotonin 5-HT$_{2C}$ receptor and 7.5-9.9 at the serotonin 5-HT$_{2A}$ receptor.

The invention is further illustrated by the following non-limiting examples:

Description 1

3-Trifluoroacetyl-2,3,4,5-tetrahydro-1H-3-benzazepine-7-sulfonyl fluoride (D1)

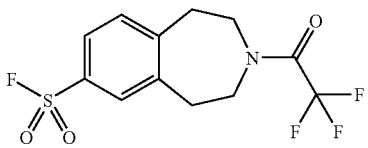

a) 3-Trifluoroacetyl-2,3,4,5-tetrahydro-1H-3-benzazepine-7-sulfonyl chloride

A solution of 3-trifluoroacetyl-2,3,4,5-tetrahydro-1H-3-benzazepine (see WO02/40471) (20 g, 80 mmol) in dichloromethane (50 mL) was added dropwise to a solution of chlorosulfonic acid (33 mL, 240 mmol) in more dichloromethane (200 mL) at 0° C. The resulting solution was stirred for 18 h without cooling then poured onto ice (250 g). The resulting organic layer was washed with brine (100 mL), dried ($MgSO_4$), and evaporated to give the subtitle compound as a white solid (23 g).

b) 3-Trifluoroacetyl-2,3,4,5-tetrahydro-1H-3-benzazepine-7-sulfonyl fluoride

A mixture of 3-trifluoroacetyl-2,3,4,5-tetrahydro-1H-3-benzazepine-7-sulfonyl chloride (23 g, 67 mmol), potassium fluoride (12 g, 200 mmol), 18-crown-6 (0.1 g), and acetonitrile (100 mL) was stirred overnight. Water (200 mL) and ethyl acetate (200 mL) were added and the organic layer was washed with brine (100 mL), dried ($MgSO_4$), and evaporated to give the title compound D1 as a white solid (21 g). $^1$H NMR 3 ($d_6$-DMSO) 3.2 (4H, m), 3.7 (4H, m), 7.6 (1H, m), and 8.0 (2H, m).

Description 2

3-Trifluoroacetyl-8-methoxy-2,3,4,5-tetrahydro-1H-3-benzazepine-7-sulfonyl fluoride (D2)

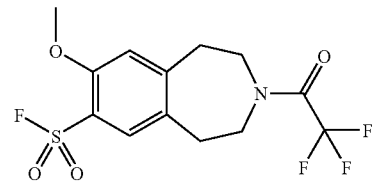

a) 3-Trifluoroacetyl-8-methoxy-2,3,4,5-tetrahydro-1H-3-benzazepine

To a mixture of 7-methoxy-2,3,4,5-tetrahydro-1H-3-benzazepine hydrochloride (see EP 285287) (5.1 g, 25 mmol), triethylamine (8.4 mL, 60 mmol), and dichloromethane (100 mL) at 0° C., was added dropwise trifluoroacetic anhydride (3.5 mL, 26 mmol). The solution was stirred for 2 h without cooling then washed with saturated aqueous sodium hydrogen carbonate (100 mL), and water (100 mL), dried ($MgSO_4$), and evaporated to give the title compound as a white solid (5.5 g).

b) 3-Trifluoroacetyl-8-methoxy-2,3,4,5-tetrahydro-1H-3-benzazepine-7-sulfonyl chloride Prepared from 3-trifluoroacetyl-8-methoxy-2,3,4,5-tetrahydro-1H-3-benzazepine using the method of Description 1(a), yield 85%.

c) 3-Trifluoroacetyl-8-methoxy-2,3,4,5-tetrahydro-1H-3-benzazepine-7-sulfonyl fluoride Prepared from 3-trifluoroacetyl-8-methoxy-2,3,4,5-tetrahydro-1H-3-benzazepine-7-sulfonyl chloride using the method of Description 1(b), yield 80%.

$^1$H NMR δ ($d_6$-DMSO) 3.1 (4H, m), 3.7 (4H, m), 4.0 (3H, s), 7.3 (1H, 2s, rotamers), and 7.8 (1H, 2s, rotamers).

Description 3

7-(3-Hydroxyphenylsulfonyl)-3-(t-butoxycarbonyl)-2,3,4,5-tetrahydro-1H-3-benzazepine (D3)

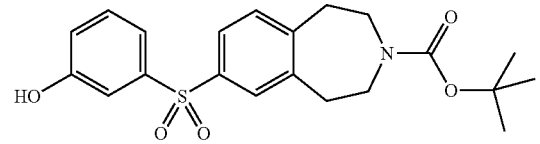

a) 7-(3-t-Butyldimethysilyloxyphenylsulfonyl)-2,3,4,5-tetrahydro-1H-3-benzazepine Prepared from 3-trifluoroacetyl-2,3,4,5-tetrahydro-1H-3-benzazepine-7-sulfonyl fluoride and 3-t-butyldimethylsilyloxybromobenzene using the method of Example 1, yield 80%.

b) 7-(3-t-Butyldimethysilyloxyphenylsulfonyl)-3-t-butoxycarbonyl)-2,3,4,5-tetrahydro-1H-3-benzazepine A solution of 7-(3-t-butyldimethysilyloxyphenylsulfonyl)-2,3,4,5-tetrahydro-1H-3-benzazepine (5.0 g, 12 mmol) in dichloromethane (100 mL) was treated with di-t-butyl dicarbonate (2.7 g, 12 mmol). After 30 min the solution was evaporated, and chromatography on silica, eluting with 10 to 50% ethyl acetate in hexane, gave the subtitle compound (5.4 g).

c) 7-(3-Hydroxyphenylsulfonyl)-3-(t-butoxycarbonyl)-2,3,4,5-tetrahydro-1H-3-benzazepine 7-(3-t-Butyldimethysilyloxyphenylsulfonyl)-3-(t-butoxycarbonyl)-2,3,4,5-tetrahydro-1H-3-benzazepine (5.4 g, 10.5 mmol) was dissolved in a solution of tetra-n-butylammonium fluoride in tetrahydrofuran (15 mL, 1M, 15 mmol). The solution was stirred for 1 h then diluted with ethyl acetate (100 mL) and washed with saturated aqueous sodium hydrogen carbonate (100 mL), and brine (100 mL), dried ($MgSO_4$), and evaporated.

Chromatography on silica, eluting with 0 to 10% methanol in dichloromethane containing 0.1M ammonia, gave the title compound D3 (3.5 g).

Description 4

8-Methoxy-3-methyl-2,3,4,5-tetrahydro-1H-3-benzazepine-7-sulfonyl fluoride (D4)

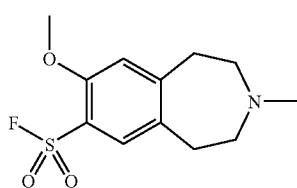

a) 7-Methoxy-3-methyl-2,3,4,5-tetrahydro-1H-3-benzazepine

A mixture of 7-methoxy-2,3,4,5-tetrahydro-1H-3-benzazepine hydrochloride (see EP 285287) (25 g, 125 mmol) and 37% formalin (25 mL) in dichloroethane (250 mL) was treated with sodium triacetoxyborohydride (30 g, 250 mmol) keeping the internal temperature below 20° C. After stirring for 2 h, water was added and the pH adjusted to 10 using 50% sodium hydroxide solution. The organic layer was separated, dried over sodium sulfate and evaporated to dryness to afford the product (23 g).

b) 8-Methoxy-3-methyl-2,3,4,5-tetrahydro-1H-3-benzazepine-7-sulfonic acid

The product from part (a) (23 g) was dissolved in trifluoroacetic acid (125 mL), and then stirred in an ice bath while chlorosulfonic acid (16.5 mL, 250 mmol) was added dropwise. The solution was stirred for 30 min, then evaporated to dryness to afford the title sulfonic acid which was used directly in the next step.

c) 8-Methoxy-3-methyl-2,3,4,5-tetrahydro-1H-3-benzazepine-7-sulfonyl chloride The sulfonic acid from part (b) was dissolved in thionyl chloride (75 mL) and the solution refluxed for 30 min. After cooling, the solution was evaporated to dryness to afford the title sulfonyl chloride which was used directly in the next step.

d) 8-Methoxy-3-methyl-2,3,4,5-tetrahydro-1H-3-benzazepine-7-sulfonyl fluoride The sulfonyl chloride from part (c) was dissolved in acetonitrile (500 mL) and potassium fluoride (37 g, 625 mmol) and 18-crown-6 (1 crystal) added. The mixture was stirred for 18 h, then quenched with cold aqueous sodium bicarbonate solution until pH=8. The mixture was extracted twice with ethyl acetate, washed with bicarbonate solution then brine, dried and evaporated to afford the sulfonyl fluoride D4 (25 g).

Description 5

7-(4-Fluoro-benzenesulfonyl)-8-methoxy-3-methyl-2,3,4,5-tetrahydro-1H-3-benzazepine (D5)

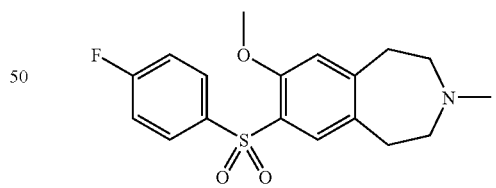

The sulfonyl fluoride D4 from Description 4 (25 g) was dissolved it dry tetrahydrofuran (250 mL) and 4-fluorophenylmagnesium bromide in tetrahydrofuran (2.5 equivalents) added over 15 min with ice bath cooling, an exotherm only apparent during the first part of the addition. Stirred overnight without cooling then added over 10 min to a solution of sodium potassium tartrate tetrahydrate (250 g) in water (450 mL) with stirring. Diethyl ether was added (400 mL) and the organic layer separated, dried, evaporated, and crystallised from diethyl ether to give crystalline fluorophenyl sulfone D5 17 g (51%).

Description 6

8-(4-Fluoro-benzenesulfonyl)-3-methyl-2,3,4,5-tetrahydro-1H-3-benzazepin-7-ol hydrobromide salt (D6)

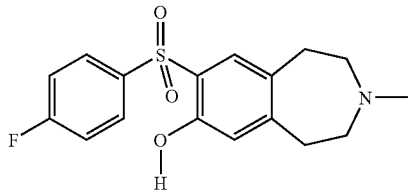

A solution of D5 (300 mg, 0.86 mmol) in aqueous 48% HBr (10 mL) was heated at 120° C. overnight. The mixture was cooled to room temperature and the solvent removed, azeotroping with toluene. Diethyl ether was added to the residue to yield the title compound D6 as the hydrobromide salt (340 mg). MH$^+$ 336. $^1$H NMR δ (DMSO-d$_6$) 2.75 (3H, d), 2.88-3.25 (6H, m), 3.50-3.66 (2H, m), 7.35-7.50 (2H, t), 7.76 (1H, s), 7.90-8.03 (2H, m), 9.85 (1H, br.s), 10.80 (1H, br.s).

Description 7

1,1,1-Trifluoro-methanesulfonic acid 8-(4-fluoro-benzenesulfonyl)-3-methyl-2,3,4,5-tetrahydro-1H-3-benzazepin-7-yl ester (D7)

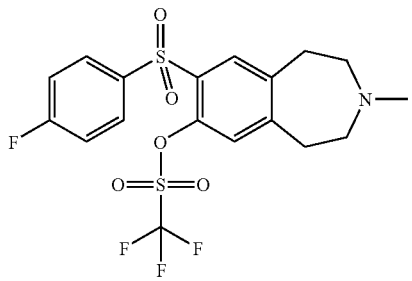

To an ice bath cooled solution of D6 (340 mg, 0.82 mmol) in acetone (10 mL) was added triethylamine (0.29 mL, 2.1 mmol) followed by trifluoromethanesulfonyl chloride (0.13 mL, 1.2 mmol). The mixture was stirred at room temperature for 2 hours. The solvent was removed and the residue partitioned between dichloromethane and saturated sodium bicarbonate. The organic layer was removed, dried (MgSO$_4$) and evaporated to yield the title compound D7 as a solid (270 mg). MH$^+$ 468. $^1$H NMR δ (CDCl$_3$) 2.42 (3H, s), 2.55-2.70 (4H, m), 2.95-3.15 (4H, m), 7.09 (1H, s), 7.15-7.24 (2H, t), 7.93-8.04 (3H, m).

Description 8

7-(4-Fluoro-benzenesulfonyl)-3,8-dimethyl-2,3,4,5-tetrahydro-1H-3-benzazepine (D8)

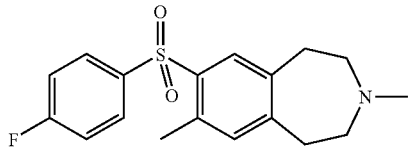

A solution of D7 (100 mg, 0.21 mmol) in dry tetrahydrofuran (2 mL) was degassed with argon for 10 minutes. To the solution Pd(PPh$_3$)$_4$ (30 mg) was added followed by methylzinc chloride (0.22 mL, 0.43 mmol) then heated at reflux for 30 minutes. The mixture was cooled to room temperature and quenched with water. Extraction with dichloromethane followed by purification by SCX and chromatography on silica gave the title compound D8 as a gum (56 mg). MH$^+$ 334. $^1$H NMR δ (CDCl$_3$) 2.36 (3H, s), 2.38 (3H, s), 2.47-2.66 (4H, m), 2.90-3.05 (4H, m), 6.96 (1H, s), 7.10-7.20 (2H, t), 7.83-7.92 (3H, m).

Description 9

2,2,2-Trifluoro-N-[4-(8-methoxy-3-methyl-2,3,4,5-tetrahydro-1H-3-benzazepine-7-sulfonyl)-phenyl]-acetamiden (D9)

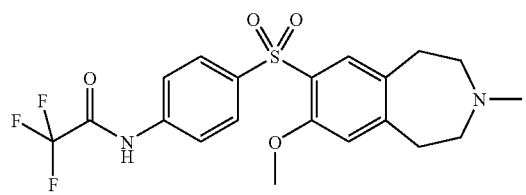

2,2,2-trifluoroacetamide (9 eq., 51.6 mmol, 5.83 g) was dissolved in dry dimethylsulfoxide (50 mL) and sodium hydride (1.01 eq., 52.1 mmol, 2.1 g) was slowly added at 0° C.; the mixture was stirred at room temperature until no more bubbling was observed. The 4-fluorosulfone D5 (2 g, 5.73 mmol), previously dissolved in dry dimethylsulfoxide (20 mL), was added to the trifluoroacetamide mixture at room temperature; the resulting reaction mixture was heated to 145° C. for 30 hours. The reaction mixture was then cooled to room temperature and it was poured onto water (400 mL); the resulting aqueous mixture was extracted with ethyl acetate (300 mL×3). The organics were washed with water (300 mL×2) and brine (200 mL×2), they were dried over Na$_2$SO$_4$, filtered and the solvent was evaporated to afford the crude product D9, 3.5 g. MH$^+$ 444.

Description 10

4-(8-Methoxy-3-methyl-2,3,4,5-tetrahydro-1H-3-benzazepine-7-sulfonyl)-phenylamine (D10)

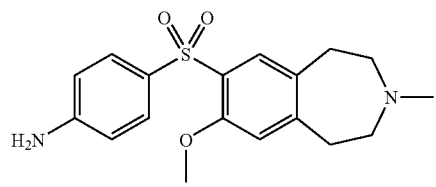

The crude trifluoroacetamide intermediate D9 (3.5 g) was dissolved in methanol (25 mL) and NaOH (2N solution) (28.5 mmol, 14.3 mL) was added at room temperature. The reaction mixture was stirred at room temperature for 14 hours and it was afterwards poured onto brine-water and the aqueous was extracted with ethyl acetate (200 mL×3); the organics were dried over Na$_2$SO$_4$, filtered and the solvent was evaporated to afford 2.6 g of crude product as a yellow solid. Chromatography on silica eluting with 0-10% MeOH—NH$_3$— DCM afforded 1.3 g of the title compound (66%), as a pale yellow solid D10. MH$^+$ 347.

Description 11

4-(8-Methoxy-3-methyl-2,3,4,5-tetrahydro-1H-3-benzazepine-7-sulfonyl)-benzaldehyde (D11)

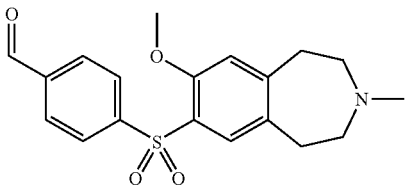

Magnesium turnings (1.4 g) in tetrahydrofuran (10 mL) were stirred under an atmosphere of argon and treated with a solution of 4-bromobenzaldehyde diethyl acetal (15.5 g) in tetrahydrofuran (60 mL) The mixture was stirred for 4 hours then the sulfonyl fluoride D4 (5.46 g) was added and the mixture was stirred for 60 hours. The mixture was poured into a solution of potassium sodium tartrate in water and extracted with ethyl acetate. The residue was purified by column chromatography 0-10% methanol (containing 0.5% aqueous ammonia)-dichloromethane. The product was treated with hydrochloric acid (10 mL) in tetrahydrofuran (100 mL) for 18 hours. The solution was basified and extracted with dichloromethane, and solvent evaporation gave the title compound D11 as a white solid. $^1$H NMR: δ CDCl$_3$ 2.38 (3H, s), 2.6 (4H, m), 2.9 (4H, m), 3.73 (3H, s) 6.65 (1H, s), 7.86 (1H, s), 8.02 (2H, d) 8.12 (2H, d), 10.12 (1H, s).

Description 12

[4-(8-Methoxy-3-methyl-2,3,4,5-tetrahydro-1H-3-benzazepine-7-sulfonyl)-phenyl]-methanol (D12)

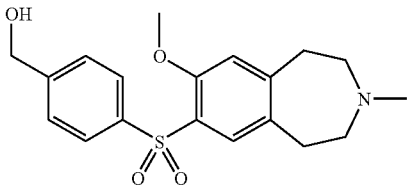

A solution of D11 (2.7 g), tetrahydrofuran (50 mL) and methanol (25 mL) was treated with sodium borohydride (0.76 g). The solution was stirred for 1 hour then treated with dilute hydrochloric acid (20 mL). The mixture was basified and extracted with dichloromethane. The solvent was evaporated and the residue was purified by column chromatography 0-10% methanol (containing 0.5% aqueous ammonia)-dichloromethane to give the title compound D12 as a white solid. (1.13 g). $^1$H NMR: δ CDCl$_3$ 2.36 (3H, s), 2.55 (4H, m), 2.93 (4H, m), 3.73 (3H, s), 4.77 (2H, s) 6.63 (1H, s), 7.47 (2H, d), 7.84 (1H, s) 7.94 (2H, d).

Description 13

7-(4-Bromobenzenesulfonyl)-8-methoxy-3-methyl-2,3,4,5-tetrahydro-1H-3-benzazepine (D13)

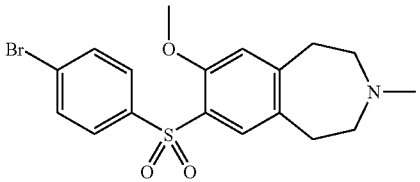

To a stirred solution of 1,4-dibromobenzene (0.665 g, 2.82 mmol, 2.0 eq) in dry tetrahydrofuran (7 mL) under argon at −78° C. was added butyllithium (1.25 mL 2.5M in hexanes, 3.10 mmol, 2.2 eq) dropwise over 10 min. After a further 30 min. a suspension of sulfonyl fluoride D4 (0.385 g, 1.41 mmol, 1.0 eq) was added portionwise. The resultant mixture was allowed to warm to room temperature then stirred for 2 h. The mixture was quenched with water (40 mL) then extracted twice with ethyl acetate (2×40 mL). The organic layer was washed sequentially with water (50 mL) and brine (50 mL) then dried over MgSO$_4$ and evaporated to dryness. Purification by Biotage chromatography, eluting with 1-6% MeOH—CH$_2$Cl$_2$ containing 0.5% NH$_3$ afforded the desired product D13 as a solid, 0.289 g (50%). MH$^+$411. $^1$H NMR δ (CDCl$_3$) 2.37 (3H, s), 2.55 (4H, m), 2.93 (4H, m), 3.75 (3H, s), 6.65 (1H, s), 7.60 (2H, d), 7.80 (3H, m).

Description 14

7-Ethoxy-8-(4-fluoro-benzenesulfonyl)-3-methyl-2,3,4,5-tetrahydro-1H-3-benzazepine (D14)

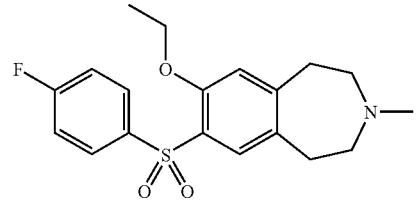

a) 7-Ethoxy-3-(t-butoxycarbonyl)-2,3,4,5-tetrahydro-1H-3-benzazepine

To a solution of 7-hydroxy-3-(t-butoxycarbonyl)-2,3,4,5-tetrahydro-1H-3-benzazepine (10 g, 38 mmol) in dimethylformamide (70 mL) was added sodium hydride (60% dispersion in oil, 1.5 g) and the resulting mixture stirred for 0.5 h. Ethyl iodide (3.6 mL, 45 mmol) was added and the mixture stirred for 12 h at 70° C. The mixture was cooled to room temperature and diluted with diethyl ether (200 mL) and water (200 mL), the layers were separated and the aqueous portion extracted with diethyl ether (200 mL). The combined organic extracts were washed with brine (200 mL) and sodium hydroxide solution (2N, 200 mL) and then evaporated to give a yellow oil.

b) 7-Ethoxy-2,3,4,5-tetrahydro-1H-3-benzazepine hydrochloride

The material from part (a) was slurried in ethanol (100 mL) and concentrated hydrochloric acid (10 mL) was added and the mixture stirred for 1 h. The solvents were removed in vacuo and the residue was treated with methanol (10 mL) and then diethyl ether (300 mL) and the resulting precipitate was filtered and dried (6.7 g).

c) 7-Ethoxy-3-methyl-2,3,4,5-tetrahydro-1H-3-benzazepine

The material from part (b) was dissolved in aqueous formalin solution (37%, 60 mL) and sodium triacetoxyborohydride (10 g) was added, the mixture was stirred for 2 h and then saturated sodium bicarbonate solution (100 mL) was added and the mixture extracted with dichloromethane (2×100 mL). The organic layers were evaporated and the residue was purified by column chromatography eluting with 10% methanol/dichloromethane. MH+ 206.

d) 7-Ethoxy-8-(4-fluoro-benzenesulfonyl)-3-methyl-2,3,4,5tetrahydro-1H-3-benzazepine The title compound D14 was prepared from part (c) in a manner similar to Descriptions 4 and 5

Description 15

7-Ethylsulfanyl-8-(4-fluoro-benzenesulfonyl)-3-methyl-2,3,4,5-tetrahydro-1H-3-benzazepine (D15)

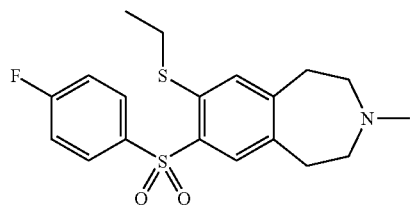

A suspension of palladium acetate (22 mg, 0.1 mmol), BINAP (92 mg, 0.15 mmol) and potassium phosphate (312 mg, 1.5 mmol) in 1,4-dioxan (4.0 mL) was sonicated for 30 minutes forming a deep, red complex.

The aryl triflate D7 from Description 7 (458 mg, 1.0 mmol) and ethane-thiol (0.25 mL, xs) were added and the mixture heated at 160° C. for 30 minutes using microwave technology (Emrys Optimizer).

The resultant was diluted with ethyl acetate (50 mL) and transferred to a separating funnel and washed with water (50 mL), then saturated aqueous sodium bicarbonate solution (50 mL). The organic layer was then dried over sodium sulfate and then evaporated in vacuo to give a crude yellow gum.

The residual gum was applied to a silica 40S biotage column and purified eluting with ethyl acetate to 20% methanol/ethyl acetate in a gradient fashion to give the title compound D15 as a yellow oil (265 mg). MH+ 380.

Description 16

2,2,2-Trifluoro-1-(6-methoxy-3,4-dihydro-1H-isoquinolin-2-yl)-ethanone (D16)

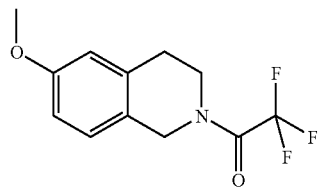

a) 6-Methoxy-1,2,3,4-tetrahydroisoquinoline hydrochloride salt

To a stirred suspension of 3-methoxyphenethylamine (50.4 g, 0.33 mol. 1.0 eq) in water (40 mL) was added 37% aqueous formaldehyde solution (27.5 mL, 1.1 eq) and stirring continued for 20 min. Concentrated HCl (80 mL) was added and the mixture heated at reflux for 1 h. After cooling to room temperature the mixture was evaporated to dryness. The residue was recrystallised from acetone, affording the desired product as a white solid (60.1 g, 90%) which was used without further purification for the next step. MH+ 164.

b) 2,2,2-Trifluoro-1-(6-methoxy-3,4-dihydro-1H-isoquinolin-2-yl)-ethanone

To an ice bath cooled mixture of 6-methoxy-1,2,3,4-tetrahydroisoquinoline hydrochloride salt from part a) (23 g, 115.2 mmol) and triethylamine (48 mL) in dichloromethane (400 mL) was added trifluoroacetic anhydride (19.5 mL). The solution was stirred for 1 hour at room temperature before quenching with saturated sodium bicarbonate. The organic layer was removed, dried (MgSO$_4$) and purified by chromatography on silica eluting with 10% EtOAc/Hexane up to 30% EtOAc/Hexane yielding the title compound D16 as a clear oil (7.75 g). MH+ 260. $^1$H NMR δ (CDCl$_3$) 2.88-2.98 (2H, t), 3.74-3.90 (5H, m), 4.63-4.75 (2H, d), 6.65-6.84 (2H, m), 7.01-7.10 (1H, m).

Description 17

6-Methoxy-2-(2,2,2-trifluoro-ethanoyl)-1,2,3,4-tetrahydro-isoquinoline-7-sulfonyl chloride (D17)

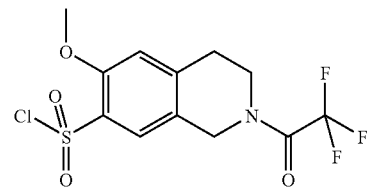

To an ice bath cooled solution of chlorosulfonic acid (1.3 mL) in dichloromethane (7.7 mL) was added D16 (0.5 g, 1.39 mmol) in dichloromethane (1.5 mL). The mixture was stirred at room temperature for 2 hours before partitioning between water and dichloromethane. The organic layer was removed, dried (MgSO$_4$) and evaporated to yield the title compound D17 (0.62 g). MH−356. $^1$H NMR δ (CDCl$_3$) 2.97-3.07 (2H, m), 3.80-3.94 (2H, m), 4.70-4.80 (2H, d), 5.29 (3H, s), 6.85-6.95 (1H, d), 7.70-7.80 (1H, d).

Description 18

6-Methoxy-2-(2,2,2-trifluoro-ethanoyl)-1,2,3,4-tetrahydro-isoquinoline-7-sulfonyl fluoride (D18)

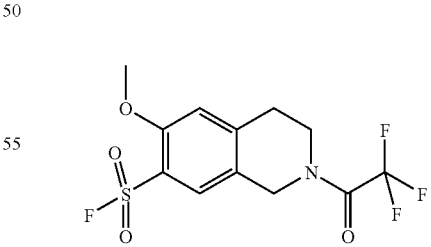

To a solution of D17 (4.06 g, 11.3 mmol) in dry acetonitrile (46 mL) was added potassium fluoride (3.45 g, 59.4 mmol) and 1 crystal of 18-crown-6. The mixture was stirred at room temperature overnight before saturated sodium bicarbonate (46 mL) was added, making the pH 8. The mixture was extracted with ethyl acetate and the organic extracts were combined and re-washed with saturated sodium bicarbonate.

The organic layer was dried (MgSO$_4$) and evaporated to give the title compound D18 as a brown solid. MH$^-$340. $^1$H NMR δ (CDCl$_3$) 2.97-3.08 (2H, m), 3.82-3.95 (2H, m), 4.01 (3H, s), 4.74-4.78 (2H, d), 6.88-6.90 (1H, d), 7.71-7.74 (1H, d).

Description 19

7-(4-Fluoro-benzenesulfonyl)-6-methoxy-1,2,3,4-tetrahydro-isoquinoline (D19)

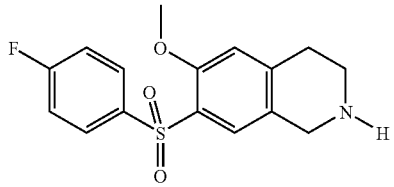

To an ice bath cooled solution of D18 (2.8 g, 8.4 mmol) in dry tetrahydrofuran (30 mL) was added dropwise 4-fluorophenylmagnesium bromide (42 mL, 1M in tetrahydrofuran). The mixture was stirred at room temperature overnight before quenching by the dropwise addition of potassium-sodium-1-tartrate tetrahydrate (35 g in 93 mL of water). Diethyl ether (60 mL) was added and the mixture gently shaken. The aqueous was re-extracted with diethyl ether and the combined organic extracts washed with brine then dried (MgSO$_4$) and evaporated. The crude mixture was purified by chromatography on silica eluting with dichloromethane up to 10% MeOH/NH$_3$/dichloromethane to yield the title compound D19 as a solid (0.94 g). MH$^+$ 322. $^1$H NMR δ (CDCl$_3$) 2.73-2.84 (2H, t), 3.08-3.17 (2H, t), 3.72 (3H, s), 4.01 (2H, s), 6.61 (1H, s), 7.05-7.18 (2H, t), 7.80 (1H, s), 7.92-8.03 (2H, m).

Description 20

7-(4-Fluoro-benzenesulfonyl)-6-methoxy-3,4-dihydro-1H-isoquinoline-2-carboxylic acid tert-butyl ester (D20)

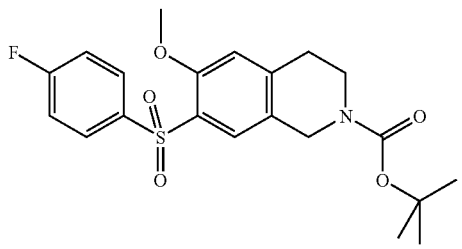

To an ice bath cooled solution of di-tert butyl dicarbonate (0.64 g, 2.93 mmol) in dry tetrahydrofuran (10 mL) was added dropwise a solution of D19 (0.94 g, 2.93 mmol) in dry tetrahydrofuran (10 mL). The mixture was stirred at room temperature for 3 hours before evaporating to dryness and partitioning between dichloromethane and brine. The organic layer was removed, dried (MgSO$_4$), and evaporated yielding the title compound D20 as a solid (0.9 g). MH$^+$322. $^1$H NMR δ (CDCl$_3$) 1.53 (9H, s), 2.78-2.87 (2H, t), 5.57-3.66 (2H, m), 3.74 (3H, s), 4.57 (2H, s), 6.65 (1H, s), 7.10-7.19 (2H, t), 7.87 (1H, s), 7.94-8.02 (2H, m).

Description 21

7-[4-(3-Fluoro-benzyloxy)-benzenesulfonyl]-methoxy-3,4-dihydro-1H-isoquinoline-2-carboxylic acid tert-butyl ester (D21)

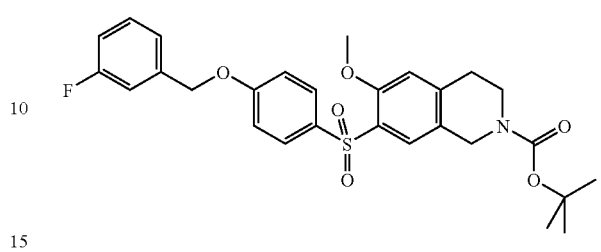

To a solution of 3-fluorobenzyl alcohol (150 mg, 1.18 mmol) in dry dimethylsulfoxide (2 mL) was added sodium hydride (34 mg, 0.83 mmol). The mixture was stirred at room temperature for 1 hour before the addition of D20 (250 mg, 0.59 mmol). The resulting mixture was heated at 80° C. overnight before allowing to cool and partitioning between ethyl acetate and water. The organic layer was removed, dried (MgSO$_4$) and purified by chromatography on silica eluting with hexane up to 50% EtOAc/hexane yielded the title compound D21 as an oil (174 mg). MH$^+$ 428. $^1$H NMR δ (CDCl$_3$) 1.49 (9H, s), 2.79-2.84 (2H, t), 3.60-3.65 (2H, t), 3.74 (3H, s), 4.56 (2H, s), 5.05-5.10 (2H, d), 6.65 (1H, s), 6.94-7.19 (5H, m), 7.30-7.43 (1H, m), 7.83-7.94 (3H, m).

Description 22

4-Methoxyphthalic acid (D22)

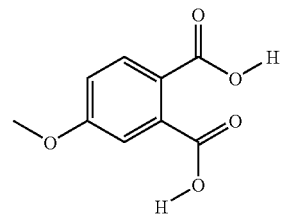

A solution of dimethyl 4-methoxyphthalate (20 g, 89 mmol) was heated at reflux in 10% aqueous sodium hydroxide (85 mL) for 1 hour. The mixture was cooled to room temperature then acidified to pH 1 using concentrated hydrochloric acid. The precipitate that formed was filtered off, washed with water and dried under vacuum to afford the title compound D22 (13.61 g). MH$^-$195. $^1$H NMR δ (DMSO-de) 3.83 (3H, s), 7.05-7.10 (3H, m), 7.72 (1H, d).

Description 23

5-Methoxy-isoindole-1,3-dione (D23)

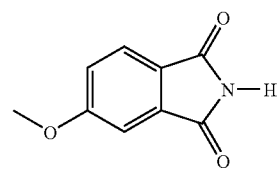

A mixture of D22 (13.61 g, 69 mmol) and urea (8.3 g, 139 mmol) were heated together in ethylene glycol (150 mL) at 180° C. for 3 hours. The mixture was cooled to room temperature and the precipitate that formed filtered off, washed with water then dried to afford the title compound D23 (6.78 g). MH⁻ 176. ¹H NMR δ(DMSO-d₆) 3.92 (3H, s), 7.27-7.38 (2H, m), 7.71-7.76 (1H, d).

Description 24

5-Methoxy-2,3-dihydro-1H-isoindole (D24)

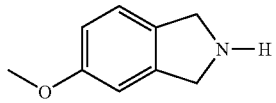

To a suspension of D23 (6.14 g, 35 mmol) in dry tetrahydrofuran (25 mL) was added dropwise BH₃-THF (100 mL, 1M in tetrahydrofuran) then heated at reflux overnight. The mixture was cooled to 0° C. then quenched by dropwise addition of methanol (10 mL). After stirring at room temperature for 20 minutes 5M HCl (10 mL) was added and the mixture heated at reflux for 1 hour. The mixture was cooled to room temperature, the pH adjusted to pH 10 by the addition of 2M NaOH (58 mL) and extracted with dichloromethane. The organic layer was dried (MgSO₄), and evaporated. Purification by SCX followed by evaporation gave the title compound D24 as an oil (1.76 g). MH⁺ 150. ¹H NMR δ (CDCl₃) 3.80 (3H, s), 4.17 (2H, s), 4.20 (2H, s), 6.75-6.83 (2H, m), 7.13 (1H, d).

Description 25

5-Methoxy-2-methyl-2,3-dihydro-1H-isoindole (D25)

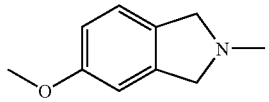

To a solution of D24 (1.76 g, 11.8 mmol), in 1,2-dichloroethane (60 mL) at room temperature was added 37% aqueous formaldehyde (20 mL, excess). After vigorous stirring for 5 minutes, sodium triacetoxyborohydride (7 g, excess) was added portionwise over a 5 minute period, the resultant solution stirred for a further 2 hours. The reaction was partitioned between saturated sodium bicarbonate and dichloromethane. The organic phase was washed with water, brine and dried (MgSO₄). The solution was evaporated to dryness and purified by SCX to give the title compound D25 as an oil (1.69 g). MH⁺ 164 ¹H NMR δ (CDCl₃) 2.57 (3H, s), 3.78 (3H, s), 3.84 (2H, s), 3.87 (2H, s), 6.71-6.74 (2H, m), 7.07 (1H, d).

Description 26

6-Methoxy-2-methyl-2,3-dihydro-1H-isoindole-5-sulfonyl fluoride (D26)

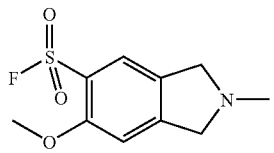

To an ice bath cooled solution of D25 (0.12 g, 0.74 mmol) in trifluoroacetic acid (0.8 mL) was added chlorosulfonic acid (0.11 mL). The mixture was stirred at room temperature for 2 hours. The solvents were removed by evaporation before thionyl chloride (1 mL) was added and the mixture heated at reflux for 1 hour. The resulting mixture was evaporated and re-dissolved in acetonitrile (6 mL) adding KF (1 g). The mixture was stirred at room temperature overnight. Saturated sodium bicarbonate and ethyl acetate were added, the organic layer was separated, dried (MgSO₄) and evaporated to dryness affording the title compound D26 as a solid (110 mg). MH⁺ 246. ¹H NMR δ (CDCl₃) 2.59 (3H, s), 3.89 (2H, s), 3.95 (2H, s), 3.99 (3H, s), 6.94 (1H, s), 7.73 (1H, s).

Description 27

5-(4-Fluoro-benzenesulfonyl)-6-methoxy-2-methyl-2,3-dihydro-1H-isoindole (D27)

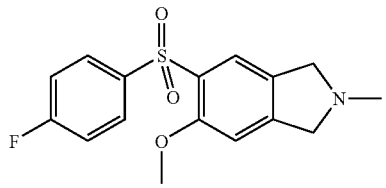

To an ice bath cooled suspension of D26 (2.36 g, 9.6 mmol) in dry tetrahydrofuran (30 mL) was added 4-fluorophenylmagnesium bromide (27 mL, 1M in tetrahydrofuran). The mixture was stirred at room temperature overnight before quenching by the dropwise addition of potassium-sodium-1-tartrate tetrahydrate (35 g in 93 mL of water). Diethyl ether (60 mL) was added and the mixture gently shaken. The aqueous was re-extracted with diethyl ether and the combined organic extracts washed with brine, dried (MgSO₄) and evaporated. The crude mixture was purified by chromatography on silica eluting with EtOAc up to 5% MeOH/NH₃/EtOAc yielding the title compound D27 as a solid (720 mg). MH⁺ 322. ¹H NMR δ (CDCl₃) 2.57 (3H, s), 3.74 (3H, s), 3.89 (4H, s), 6.75 (1H, s), 7.10-7.20 (2H, t), 7.90-8.03 (3H, m).

Description 28

[8-(4-Bromo-benzenesulfonyl)-3-methyl-2,3,4,5-tetrahydro-1H-3-benzazepin-7-yl]-dimethyl-amine (D28)

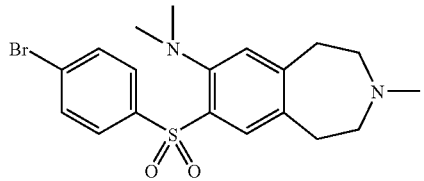

a) 7-Amino-8-iodo-1,2,4,5-tetrahydro-3-benzazepine-3-carboxylic acid tert-butyl ester A solution of 7-amino-1,2,4,5-tetrahydro-3-benzazepine-3-rboxylic acid tert-butyl ester (5 g, 3.8 mmol) (see WO98/30560) in dichloromethane/methanol (300/150 ml) was added benzyl trimethylammonium iodine dichloride (6.6 g, 3.8 mmol) and calcium carbonate (2.9 g). The mixture was stirred at room temperature for 30 mins and then evaporated in vacuo. The residue was partitioned between diethyl ether (100 ml) and 5% sodium sulfite solution (200 ml) and the layers separated and the organic portion evaporated to give the subtitled compound (6.2 g) MH+ 389.

b) 7-Dimethylamino-8-Iodo-1,2,4,5-tetrahydro-3-benzazepine-3-carboxylic acid tert-butyl ester 7-Amino-8-iodo-1,2,4,5-tetrahydro-3-benzazepine-3-carboxylic acid tert-butyl ester was dimethylated using an analogous procedure to Example E2 to give the subtitled compound. MH+ 417.

c) (4-Bromo-phenylsulfanyl)-dimethylamino-1,2,4,5-tetrahydro-3-benzazepine-3-carboxylic acid tert-butyl ester 7-Dimethylamino-8-iodo-1,2,4,5-tetrahydro-3-benzazepine-3-carboxylic acid tert-butyl ester (100 mg, 0.24 mmol), copper(I) iodide (2.3 mg) and potassium phosphate (102 mg) were stirred under an argon atmosphere in ethylene glycol (3 ml). 4-Bromophenylthiol (68 mg) was added and the mixture heated at 160° C. for 30 mins in a microwave reactor. The mixture was treated with sodium bicarbonate solution and extracted with dichloromethane (2×50 ml) and the combined organic extracts were treated with di-tert butyl dicarbonate and triethylamine to convert any deprotected material back to the protected form. Sodium bicarbonate/dichloromethane workup gave the desired product (125 mg) MH+ 478.

d) (4-Bromo-benzenesulfonyl)-dimethylamino-1,2,4,5-tetrahydro-3-benzazepine-3-carboxylic acid dimethyl-ethyl ester (4-Bromo-phenylsulfanyl)-dimethylamino-1,2,4,5-tetrahydro-3-benzazepine-3-carboxylic acid tert-butyl ester (2.8 g, 6.0 mmol) in dichloromethane (5 ml) was added to magnesium monoperoxyphthalate hexahydrate (MMPP) (7.4 g, 80%) in dichloromethane (20 ml) and methanol (3 ml) at 0° C. dropwise. After addition the mixture was allowed to warm to room temperature and stirred for 1 h then a further portion of MMPP (1 g) was added and stirred for a further 1 h. Sodium sulfite solution (10%, 300 ml) was added and the mixture stirred thoroughly for 30 min). Water (3 L) and dichloromethane (400 ml) were then added and the organic layer separated and washed with sodium bicarbonate solution (500 ml), water (2×1 L) and brine (500 ml) then evaporated in vacuo. Chromatography on silica eluting with 0-20% ethyl acetate/hexane afforded 3.22 g of the subtitled compound. MH+ 510.

e) [8-(4-Bromo-benzenesulfonyl)-3-methyl-2,3,4,5-tetrahydro-1H-3-benzazepin-7-yl]-dimethyl-amine (D28)

(4-Bromo-benzenesulfonyl)-dimethylamino-1,2,4,5-tetrahydro-3-benzazepine-3-carboxylic acid dimethyl-ethyl ester was converted to the title compound by using an analogous procedure to descriptions D14b and D14c to give the subtitled compound D28. MH+ 424.

Description 29

7-(4-Fluoro-benzenesulfonyl)-8-isopropoxy-3-methyl-2,3,4,5-tetrahydro-1H-3-benzazepine (D29)

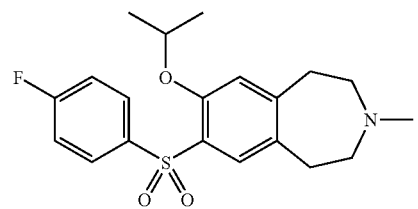

The phenol (D6) (1.1 g), triphenylphosphine (1.7 g) and isopropanol (0.5 ml) were dissolved in tetrahydrofuran and cooled to 0° C., Diisopropyl azodicarboxylate (1.3 ml) was added dropwise and the mixture stirred at room temperature for 1 h. The mixture was passed through an SCX column and then chromatography on silica eluting with 4% methanol/dichloromethane afforded the titled compound D29 (870 mg) MH+ 365

Description 30

[8-(4-Fluoro-benzenesulfonyl)-3-methyl-2,3,4,5-tetrahydro-1H-3-benzazepin-7-yl]-dimethyl-amine (D30)

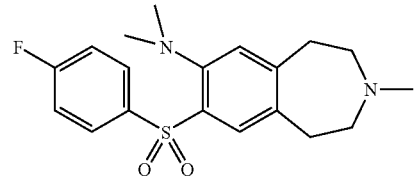

a) 7-Dimethylamino-8-(4-fluoro benzenesulfonyl)-1,2,4,5-tetrahydro-3-benzazepine-3-carboxylic acid dimethyl-ethyl ester Iodide (D28b) (7 g) and 4-fluorophenylsulfonylfluoride (6 g) were cooled to −78° C. in tetrahydrofuran (80 ml) under an argon atmosphere. n-Butyllithium (2.5M, 14 ml) was added dropwise and the mixture stirred for 1 h at −78° C. and then quenched with water (20 ml) and dichloromethane (30 ml). The organic layer was separated and evaporated to give the crude product. Chromatography on silica eluting with 7-20% ethyl acetate/pentane afforded the subtitled compound (5.6 g) MH+ 449.

b) [8-(4-Fluoro-benzenesulfonyl)-3-methyl-2,3,4,5-tetrahydro-1H-3-benzazepin-7-yl]-dimethyl-amine 7-Dimethylamino-8-(4-fluoro-benzenesulfonyl)-1,2,4,5-tetrahydro-3-benzazepine-3-carboxylic acid dimethyl-ethyl ester was converted to the title compound by using an analogous procedure to descriptions D14b and D14c to give the title compound D30. MH+ 349.

Description 31

6-Ethoxy-7-(4-fluoro-benzenesulfonyl)-1,2,3,4-tetrahydro-isoquinoline (D31)

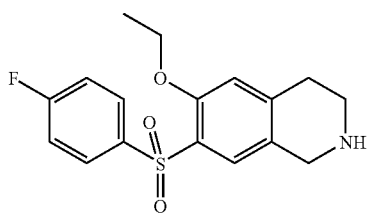

a) 3-Ethoxy-benzaldehyde

To a solution of 2-hydroxybenzaldehyde (20 g, 163 mmol) in acetone (250 mL) was added anhydrous potassium carbonate (33 g, 239 mmol) followed by ethyl iodide (17 mL, 211 mmol). The mixture was heated at reflux for 12 hours. After cooling to room temperature water and ethyl acetate were added. The organic layer was removed, dried over $MgSO_4$ and evaporated to dryness yielding the subtitled compound as a yellow oil (22.10 g). $^1$H NMR δ ($CDCl_3$) 1.40-1.50 (3H, t), 4.02-4.15 (2H, q), 7.13-7.22 (1H, m), 7.36-7.48 (3H, m), 9.97 (1H, s).

b) 1-Ethoxy-3-(2-nitro-ethyl)-benzene

A mixture of nitromethane (0.36 mL, 6.7 mmol) and 3-ethoxy-benzaldehyde (1 g, 6.7 mmol) in methanol (1.4 mL) was cooled to −10° C. To this mixture sodium hydroxide (0.28 g in 1 mL water) was added dropwise. The temperature during addition was maintained around 10° C. After 1 hour a yellow precipitate formed and water (5 mL) was added. The resulting solution was added to HCl (4M, 3 mL). The precipitate that formed was filtered off and washed with water. Purification by chromatography on silica, eluting with 1 to 15% ethyl acetate in hexane, gave the subtitled compound as a yellow solid (0.49 g). $^1$H NMR δ ($CDCl_3$) 1.40-1.48 (3H, t), 4.01-4.13 (2H, q), 6.97-7.06 (2H, m), 7.09-7.15 (1H, d), 7.30-7.40 (1H, t), 7.53-7.62 (1H, d), 7.91-8.00 (1H, d).

c) 2-(3-Ethoxy-phenyl)-ethylamine

To a solution of $LiAlH_4$ (1M in THF, 13 mL) was added dropwise a solution of 1-ethoxy-3-(2-nitro-ethyl)-benzene (0.5 g, 2.6 mmol) in THF (8 mL). The mixture was refluxed for two hours before allowing to cool and adding dropwise to rochelles salt. The mixture was extracted with ethyl acetate, dried with sodium sulfate and evaporated to dryness. The resulting yellow oil was purified by chromatography on silica, eluting with 3 to 15% MeOH/$NH_3$ in dichloromethane, yielding the subtitled compound as a yellow oil (0.23 g).

$MH^+$166. $^1$H NMR δ ($CDCl_3$) 1.31-1.43 (3H, t), 2.66-2.76 (2H, t), 2.90-3.00 (2H, t), 3.96-4.10 (2H, q), 6.70-6.80 (3H, m), 7.15-7.26 (1H, m).

d) 6-Ethoxy-1,2,3,4-tetrahydro-isoquinoline

A stirred mixture of 2-(3-ethoxy-phenyl)-ethylamine (7.0 g, 42 mmol) and 37% aqueous formaldehyde solution (3.5 mL) was heated at 110° C. for 30 minutes. The stirring was stopped and the upper water layer was removed by pipette. To the resulting mixture water (5.25 mL) and concentrated HCl (10.5 mL) were added followed by heating 100° C. for 30 minutes. After allowing to cool to room temperature the mixture was evaporated to dryness and recrystallised from acetone yielding the subtitled compound as a cream solid (2.73 g). $MH^+$ 178. $^1$H NMR δ (DMSO) 1.27-1.35 (3H, t), 2.88-3.03 (2H, t), 3.18-3.40 (2H, br, t), 3.95-4.08 (2H, q), 4.10-4.22 (2H, m), 6.74-6.85 (2H, m), 7.05-7.15 (1H, m), 9.33-9.55 (2H, br.s).

e) 1-(6-Ethoxy-3,4-dihydro-1H-isoquinolin-2-yl)-2,2,2-trifluoro-ethanone

To a solution of 6-ethoxy-1,2,3,4-tetrahydro-isoquinoline (2.52 g, 14.2 mmol) and triethylamine (6 mL) in dichloromethane (50 mL) at 0° C. was added dropwise trifluoroacetic anhydride (2.4 mL, 17 mmol). The mixture was stirred at room temperature for 1 hour before washing with saturated sodium bicarbonate. The organic layer was removed, dried over sodium sulfate and evaporated to dryness. The resulting oil was purified by chromatography on silica, eluting with 10 to 30% ethyl acetate in hexane to yield the subtitled compound as a clear oil (2.50 g). $MH^+$ 274. $^1$H NMR δ ($CDCl_3$) 1.35-1.45 (3H, t), 2.84-2.95 (2H, m), 3.75-3.89 (2H, m), 3.96-4.10 (2H, q), 3.65-3.77 (2H, d), 3.65-3.83 (2H, m), 6.97-7.08 (1H, t).

f) 6-Ethoxy-2-(2,2,2-trifluoro-ethanoyl)-1,2,3,4-tetrahydro-isoquinoline-7-sulfonyl chloride To a solution of chlorosulfonic acid (0.48 mL) in dichloromethane (5 mL) at 0° C. was added dropwise a solution of 1-(6-ethoxy-3,4-dihydro-1H-isoquinolin-2-yl)-2,2,2-trifluoro-ethanone (0.39 g, 1.43 mmol). The mixture was stirred at room temperature overnight before partitioning between water and dichloromethane. The organic layer was removed, dried over sodium sulfate, filtered and evaporated to dryness yielding the subtitled compound as a clear oil (0.34 g). $^1$H NMR δ ($CDCl_3$) 1.46-1.63 (3H, t), 2.95-3.06 (2H, m), 3.80-3.95 (2H, m), 4.18-4.32 (2H, m), 4.69-4.80 (2H, d), 6.84-6.93 (1H, d), 7.70-7.79 (1H, d).

g) 6-Ethoxy-2-2,2,2-trifluoro-ethanoyl)-1,2,3,4-tetrahydro-isoquinoline-7-sulfonyl fluoride To a solution of 6-ethoxy-2-(2,2,2-trifluoro-ethanoyl)-1,2,3,4-tetrahydro-isoquinoline-7-sulfonyl chloride (0.34 g, 0.92 mmol) in acetonitrile (3.8 mL) was added potassium fluoride (0.28 g, 4.8 mmol) and 18-crown-16 (1 crystal). The mixture was stirred at room temperature overnight before addition of aqueous sodium bicarbonate to pH 8. The resulting mixture was extracted with ethyl acetate, dried over $MgSO_4$ and evaporated to dryness yielding the subtitled compound as a white solid (0.29 g). $MH^-$354. $^1$H NMR δ ($CDCl_3$) 1.43-1.53 (3H, t), 2.95-3.07 (2H, m), 3.80-3.93 (2H, m), 4.14-4.26 (2H, m), 4.70-4.80 (2H, d), 6.82-6.90 (1H, d), 7.68-7.75 (1H, d).

h) 6-Ethoxy-7-(4-fluoro-benzenesulfonyl)-1,2,3,4-tetrahydro-isoquinoline

To an ice bath cooled solution of 6-ethoxy-2-(2,2,2-trifluoro-ethanoyl)-1,2,3,4-tetrahydro-isoquinoline-7-sulfonyl fluoride (1.30 g, 3.66 mmol) in THF (13 mL) was added dropwise 4-fluorophenylmagnesium bromide (18.3 mL, 18.3 mmol). The mixture was stirred at room temperature overnight before quenching with aqueous sodium potassium tartrate tetrahydrate (13 g). The aqueous was extracted twice with diethyl ether. The organics were combined, dried and evaporated to dryness. The resulting oil was purified by chromatography on silica, eluting with 1 to 10% MeOH/NH$_3$ in dichloromethane to yield the title compound D31 as a solid (700 mg). MH$^+$ 336. $^1$H NMR δ (CDCl$_3$)1.22-1.37 (3H, t), 2.74-2.91 (2H, m), 3.08-3.19 (2H, t), 4.01 (2H, s), 4.13-4.25 (2H, m), 6.58 (1H, s), 7.06-7.20 (2H, m), 7.83 (1H, s), 7.91-8.01 (2H, m).

Description 32

(4-Bromo-phenyl)-(3-methoxy-benzyl)-methyl-amine (D32)

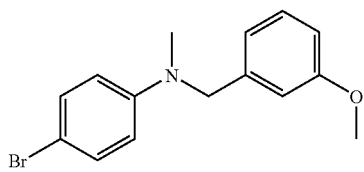

a) N-(4-Bromo-phenyl)-formamide

Formic acid (7 mL, 186 mmol) and acetic anhydride (140.1 mL, 150 mmol) were heated together at 55° C. for 2 hours. The mixture was cooled to room temperature, THF (11 mL) was added followed by 4-bromoaniline (10 g, 58 mmol) in THF (20 mL). The mixture was stirred at room temperature for 3 hours before evaporating to dryness. Trituration of the solid gave the subtitled compound as a light brown solid (8.22 g). MH$^-$ 198/200. $^1$H NMR δ (CDCl$_3$) 6.93-7.04 (2H, d), 7.24 (2H, s), 8.59-8.70 (1H, d).

b) (4-Bromo-phenyl)-methyl-amine

To a solution of N-(4-Bromo-phenyl)-formamide D32a (8.2 g, 41 mmol) in dry THF (100 mL) was added BF$_3$.Et$_2$O (8.2 mL, 61 mmol). The mixture was heated to reflux and BH$_3$.THF (103 mL, 103 mmol) added dropwise, the mixture was heated for a further 2 hours. After cooling to room temperature concentrated HCl (100 mL) was added and the mixture stirred for one hour. The pH of the mixture was adjusted to pH 13 using concentrated NaOH. Extraction with ether, drying over MgSO$_4$ and evaporating to dryness gave the subtitled compound as light brown oil (7.58 g). MH$^+$ 186/188. $^1$H NMR δ (CDCl$_3$) 2.81 (3H, s), 3.63-3.78 (1H, br.s), 6.43-6.52 (2H, d), 7.22-7.30 (2H, d).

c) (4-Bromo-phenyl)-(3-methoxy-benzyl)-methyl-amine

To a solution of D32b (300 mg, 1.6 mmol) in 1,2 dichloroethane (10 mL) was added m-anisaldehyde (0.39 mL, 3.2 mmol). After stirring at room temperature for 10 minutes sodium triacetoxyborohydride (678 mg, 3.2 mmol) was added. The mixture was stirred at room temperature overnight before quenching with saturated sodium bicarbonate. Extraction of the crude mixture with dichloromethane followed by chromatography on silica, eluting with 0 to 20% ethyl acetate in hexane yielded the title compound (D32) as a clear oil (300 mg). MH$^+$ 308/306. $^1$H NMR δ (CDCl$_3$) 3.00 (3H, s), 3.76 (3H, s), 4.47 (2H, s), 6.53-6.64 (2H, d), 6.72-6.84 (3H, m), 7.18-7.32 (3H, m).

Description 33

7-[4(tert-Butyldimethylsilyloxymethyl)benzenesulfonyl]-6-methoxy-1,2,3,4-tetrahydroisoquinoline (D33)

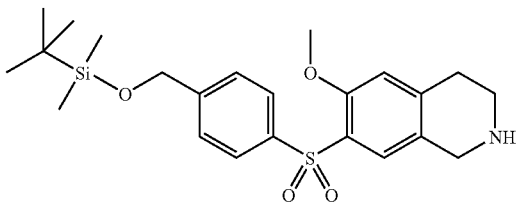

To a stirred solution of (4-bromobenzyloxy)tert-butylidimethylsilane (8.74 g, 29.0 mmol, 5.0 eq) [prepared according to the procedure by Boaz et al, J. Org. Chem.; 1993, 58, 3042-3045] in THF (50 ml) under argon at −78° C. was added dropwise butyllithium (12.0 ml 2.5M in hexanes, 30.2 mmol, 5.2 eq). After 30 mins at −78° C. a solution of sulfonyl fluoride D18 (1.98 g, 5.80 mmol, 1.0 eq) in THF (15 ml) was added dropwise. The resultant red solution was stirred for a further 1 h then quenched at −78° C. by the addition of glacial acetic acid (4 ml) followed by water (50 ml) and the mixture allowed to warm to room temperature. The pH was adjusted to 7 with saturated NaHCO$_3$ solution then extracted with ethyl acetate (2×100 ml). The organic solution was washed with water (100 ml), brine (100 ml), dried over MgSO$_4$ and concentrated to dryness. Purification by biotage chromatography, eluting with 5-10% MeOH—CH$_2$Cl$_2$ containing 0.2% NH$_3$ afforded the desired product as a white solid (2.46 g, 84%). MH$^+$ 448. $^1$H NMR: δ CDCl$_3$ 0.10 (6H, s), 0.94 (9H, s), 2.79 (2H, t), 3.12 (2H, t), 3.71 (3H, s), 4.02 (2H, s), 4.78 (2H, s), 6.60 (1H, s), 7.42 (2H, d), 7.81 (1H, s), 7.91 (2H, d).

Description 34

7-[4-(tert-Butyldimethylsilyloxymethyl)benzenesulfonyl]6-methoxy-3,4-dihydro-1H-isoquinoline-2-carboxylic acid tert-butyl ester (D34)

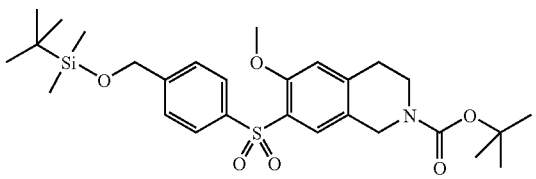

To a solution of the amine D33 (2.21 g, 4.94 mmol, 1.0 eq) in dichloromethane (45 ml) at room temperature was added triethylamine (0.70 g, 6.92 mmol, 1.4 eq) and solid (Boc)$_2$O (1.29 g, 5.92 mmol, 1.2 eq). After 16 h at room temperature water was added (100 ml) and the layers separated. The aqueous layer was extracted with more dichloromethane (50 ml) and the combined organic layer washed with brine (100 ml), dried over MgSO$_4$ and evaporated to dryness. Purification by biotage chromatography, eluting with 30-50% EtOAc-hexane afforded the desired product D34 as a white solid (2.56 g, 95%). MH$^+$ not observed. $^1$H NMR: δ CDCl$_3$ 0.10 (6H, s), 0.94 (9H, s), 1.50 (9H, s), 2.82 (2H, t), 3.63 (2H, t), 3.73 (3H, s), 4.58 (2H, s), 4.79 (2H, s), 6.64 (1H, s), 7.43 (2H, d), 7.90 (1H, s), 7.92 (2H, d).

Description 35

7-(4-Hydroxymethyl-benzenesulfonyl)-6-methoxy-3,4-dihydro-1H-isoquinoline-2-carboxylic acid tert-butyl ester (D35)

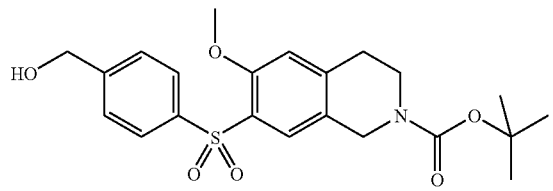

To a stirred solution of silyl ether D34 (2.49 g, 4.55 mmol, 1.0 eq) in THF (30 ml) was added Bu$_4$NF (5.0 ml 1M solution in THF, 5.00 mmol, 1.1 eq). After 30 min at room temperature, water (50 ml) and EtOAc (50 ml) were added and the layers separated. The organic solution was washed with brine (50 ml), dried over MgSO$_4$ and concentrated to dryness. The residual solid was triturated three times with hexane to remove tert-butyldimethylsilyl fluoride then dried in vacuo, giving a white solid which required no further purification (1.90 g, 96%). MH$^+$ not observed. $^1$H NMR: δ CDCl$_3$ 1.50 (9H, s), 2.82 (2H, t), 3.63 (2H, t), 3.73 (3H, s), 4.58 (2H, s), 4.78 (2H, s), 6.64 (1H, s), 7.47 (2H, d), 7.88 (1H, s), 7.94 (2H, d).

Description 36

7-[4-(4-Chlorophenoxymethyl)benzenesulfonyl]-6-methoxy-3,4-dihydro-1H-isoquinoline-2-carboxylic acid tert-butyl ester (D36)

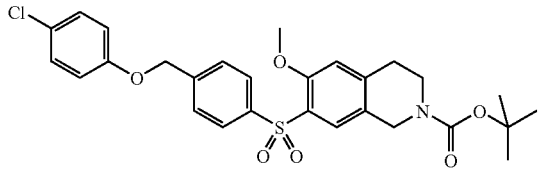

To a stirred solution of the alcohol D35 (0.177 g, 0.408 mmol, 1.0 eq), triphenylphosphine (0.118 g, 0.449 mmol, 1.1 eq) and 4-chlorophenol (0.058 g, 0.449 mmol, 1.0 eq) in THF (3 ml) under argon at 0° C. was added dropwise diisopropyl azodicarboxylate (88 ul, 0.449 mmol, 1.1 eq). When addition was complete, the mixture was allowed to warm to room temperature and stirred for 3 h. Water (20 ml) and EtOAc (20 ml) were added and the layers separated. The aqueous layer was extracted with more EtOAc (20 ml) and the combined organic layer washed with brine (40 ml), dried over MgSO$_4$ and concentrated to dryness. Purification by biotage chromatography, eluting with 30-50% EtOAc-hexane afforded the desired product as a colourless oil (0.179 g, 81%). M-Boc$^+$ 444. $^1$H NMR: δ CDCl$_3$ 1.50 (9H, s), 2.83 (2H, t), 3.63 (2H, t), 3.73 (3H, s), 4.58 (2H, s), 5.09 (2H, s), 6.65 (1H, s), 6.87 (2H, d), 7.24 (2H, d), 7.52 (2H, d), 7.89 (1H, s), 7.98 (2H, d).

Description 37

3-Methyl-7-(4-fluorophenylsulfonyl)-9-phenyl-1,2,4,5-tetrahydro-3-benzazepine (D37)

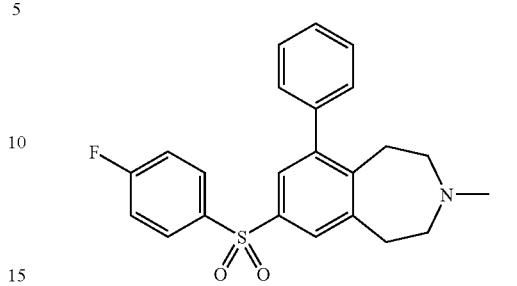

a) 3-Trifluoroacetyl-9-iodo-1,2,4,5-tetrahydro-3-benzazepine-7-sulfonyl fluoride To a solution of 3-trifluoroacetyl-1,2,4,5-tetrahydro-3-benzazepine-7-sulfonyl fluoride (D1) (5.3 g, 17 mmol) in trifluoromethanesulfonic acid (30 ml) at 0° C. was added portionwise N-iodosuccinimide (5.9 g, 25 mmol). The resulting solution was stirred for 1 h without cooling then poured into saturated aqueous sodium hydrogencarbonate (200 ml) containing sodium sulfite (1 g), extracted with ethyl acetate (100 ml), and the resulting organic layer washed with brine (100 ml), dried (MgSO$_4$), and evaporated. Chromatography on silica, eluting with 3:1 hexane:ethyl acetate gave the subtitle compound as a white solid (5.2 g).

b) 7-(4-Fluorophenylsulfonyl)-9-iodo-1,2,4,5-tetrahydro-3-benzazepine

To a solution of 3-trifluoroacetyl-9-iodo-1,2,4,5-tetrahydro-3-benzazepine-7-sulfonyl fluoride (5.29, 11.5 mmol) in tetrahydrofuran (50 ml) was added 4-fluorophenylmagnesium chloride (50 ml, 1M in tetrahydrofuran, 50 mmol). The resulting solution was stirred for 18 h without cooling then poured into saturated aqueous sodium potassium tartrate (150 ml), and extracted with diethyl ether (100 ml), The resulting organic layer washed with brine (100 ml), dried (MgSO$_4$), and evaporated. Isolation using an SCX column and crystallisation from diethyl ether gave the subtitle compound as a white solid (2.4 g).

c) 3-Methyl-7-(4-fluorophenylsulfonyl)-9-iodo-1,2,4,5-tetrahydro-3-benzazepine

To a solution of 7-(4-fluorophenylsulfonyl)-9-iodo-1,2,4,5-tetrahydro-3-benzazepine (2.4 g, 5.5 mmol) in dichloromethane (20 ml) were added sodium triacetoxyborohydride (1.8 g, 8.5 mmol) and formalin (1 ml, 37%, 12 mmol). The mixture was stirred for 2 h without cooling then poured into water (100 ml) and extracted with more dichloromethane (100 ml). The resulting organic layer was washed with brine (100 ml), dried (MgSO$_4$), and evaporated to give the subtitle compound as a white foam (2.4 g).

d) 3-Methyl-7-(4-fluorophenylsulfonyl)-9-phenyl-1,2,4,5-tetrahydro-3-benzazepine A mixture of 3-methyl-7-(4fluorophenylsulfonyl)-9-iodo-1,2,4,5-tetrahydro-3-benzazepine (0.9 g, 2 mmol), phenylboronic acid (0.4 g, 3 mmol), potassium carbonate (1.6 g, 12 mmol), ethanol (6 ml), water (6 ml), and toluene (25 ml) was degassed, then tetrakis(triphenylphosphine)palladium (0) (100 mg) was added and the mixture heated at 60° C. for 18 h. After cooling the mixture was poured into water (50 ml) and extracted with more ethyl acetate (50 ml). The resulting organic layer washed with brine (100 ml), dried (MgSO$_4$), and evaporated. Isolation using an SCX column and subsequent chromatography on silica eluting with 0 to 10% methanol in dichloromethane containing 0.1M ammonia, gave the title compound as a white foam (0.6 g). $^1$H NMR δ (d$_6$-DMSO) 2.2 (3H, s), 2.5 (4H, m), 2.8 (2H, m), 3.1 (2H, m), 7.2 (2H, m), 7.4 (5H, m), 7.6 (1H, s), 7.8 (1H, s), and 8.1 (2H, m).

EXAMPLE 1

7-Methoxy-8-(3-phenoxy-benzenesulfonyl)-2,3,4,5-tetrahydro-1H-3-benzazepine hydrochloride (E1)

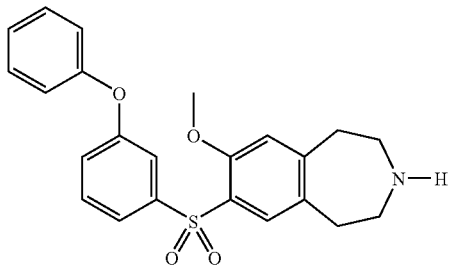

A solution of 3-phenoxy-bromobenzene (1.5 g, 6 mmol) in tetrahydrofuran (10 mL) at −78° C. was treated with tert-butyllithium (6 mL, 1.7M in pentane, 10.2 mmol). After 20 min at −78° C., a solution of D2 (0.53 g, 1.5 mmol) in tetrahydrofuran (10 mL) was added, and after a further 30 min stirring without cooling, water (50 mL) and ethyl acetate (50 mL) were added. The organic layer was washed with brine, dried (MgSO$_4$), and evaporated. Chromatography on silica, eluting with 6% methanol in dichloro-methane containing 0.5% ammonia, gave the title compound E1 (0.2 g) isolated as the hydrochloride salt from ether. MH$^+$ 409. $^1$H NMR δ (CDCl$_3$) 2.93 (8H, s), 3.70 (3H, s), 6.45 (1H, s), 7.02 (2H, d), 7.20 (2H, m), 7.38 (3H, m), 7.64 (2H, m), 7.80 (1H, s).

EXAMPLE 2

7-Methoxy-3-methyl-8-(3-phenoxy-benzenesulfonyl)-2,3,4,5-tetrahydro-1H-3-benzazepine hydrochloride (E2)

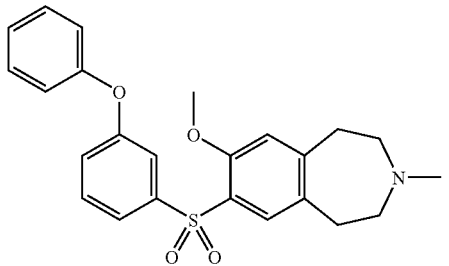

A mixture of E1 hydrochloride salt (0.2 g, 0.5 mmol), sodium triacetoxyborohydride (400 MG), aqueous formaldehyde (0.5 mL, 37%), and 1,2-dichloroethane (10 mL containing 0.5 mL triethylamine) was stirred for 18 h then diluted with dichloromethane (50 mL) and washed with saturated aqueous sodium hydrogen carbonate (100 mL), dried (MgSO$_4$), and evaporated to give the title compound E2 isolated as the hydrochloride salt from ether (0.3 g). MH$^+$ 423.

$^1$H NMR δ (CDCl3) 2.39 (3H, s), 2.60 (4H, m), 2.97 (4H, m), 3.70 (3H, s), 6.65 (1H, s), 6.99 (2H, d), 7.20 (2H, m), 7.38 (3H, m), 7.63 (2H, m), 7.81 (1H, s).

EXAMPLE 3

7-(3-Benzyloxyphenylsulfonyl)-2,3,4,5-tetrahydro-1H-3-benzazepine hydrochloride (E3)

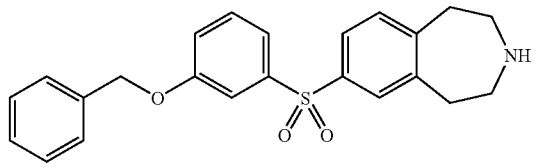

a) 7-(3-Benzyloxyphenylsulfonyl)-3-(t-butoxycarbonyl)-2,3,4,5-tetrahydro-1H-3-benzazepine A solution of D3 (270 mg, 0.67 mmol) in dimethylformamide (5 mL) was treated with 60% sodium hydride (40 mg) at 0° C., then allowed to warm to room temperature. Benzyl bromide (137 mg, 0.8 mmol) in dimethylformamide (2 mL) was added, and the solution stirred overnight. The mixture was then poured onto water and extracted with ethyl acetate. The combined organic layers were washed with brine dried and evaporated. Chromatography on silica, eluting with 40% ethyl acetate in hexane afforded the product (200 mg). MH$^+$ 494.

b) 7-(3-Benzyloxyphenylsulfonyl)-2,3,4,5-tetrahydro-1H-3-benzazepine hydrochloride A solution of E3a (200 mg) in ether (1 mL) was treated with HCl in dioxan (12 mL; 4M). After 2 h, ether was added and the precipitate filtered and dried to afford the title compound E3 (186 mg). MH$^+$ 394.

Examples 4-30 were prepared using analogous procedures to Examples 1, 2 and 3 products were isolated as either the free bases or hydrochloride salts. All $^1$H NMR are consistent with the structures shown.

EXAMPLE 31

7-[4-(4-Chloro-benzyloxy)-benzenesulfonyl]-8-methoxy-3-methyl-2,3,4,5-tetrahydro-1H-3-benzazepine hydrochloride (E31)

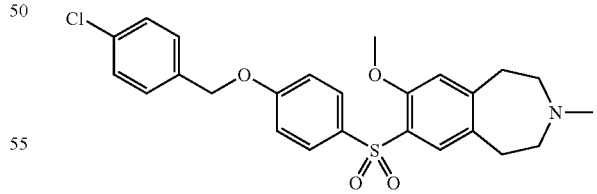

Sodium hydride (60% in oil) (2.52 g, 63 mmol) was suspended in dry dimethylsulfoxide (30 mL) and 4-chlorobenzyl alcohol (12 g, 84 mmol) in dry dimethylsulfoxide (30 mL) was added over 15 min by syringe keeping the temperature below 30° C. (internal). This solution was stirred for 15 minutes to give a grey clear solution. The fluorosulfone D5 (15 g) was then added as a solid portionwise over 10 minutes keeping the temperature below 35° C. and the solution was stirred until the temperature began to fall, (approximately 10 minutes). The solution was then heated to 40° C. and stirred at this temperature for 1.5 hours with monitoring by LC and MS. The reaction mixture was then poured into 2M HCl (600 mL) and extracted with ethyl acetate (400 mL×1 and 250 mL×2) [this extraction was done by decantation into a separating funnel as leaving the oil which had precipitated in the conical flask along with some aqueous]. The ethyl acetate extracts were washed with a mixture of water 200 mL, brine 20 mL and 2M HCl 10 mL. The combined aqueous layers were cooled and basified with 12.5M sodium hydroxide and extracted with ethyl acetate (400 mL×1 and 250 mL×2), washed with brine and dried over sodium sulfate. The solvent was removed to give the title compound E31 (free base) as a cream coloured solid (18.24 g). A combined batch of 35.6 g of the free base was recrystallised from ethanol (following the addition of ethereal hydrogen chloride) which afforded the title compound E31 as the hydrochloride salt 30.6 g. MH+ 471. $^1$H NMR δ(DMSO) 2.78 (3H, s), 2.9-3.2 (4H, m), 3.2-3.6 (4H, m), 3.73 (3H, s), 5.19 (2H, s), 7.08 (1H, s), 7.18 (2H, d), 7.47 (4H, s), 7.79-7.83 (3H, m).

Examples 32-74 161 and 162 were prepared from D5 (or the appropriate $R^4$ substituted D5) and the appropriate alcohol using an analogous procedure to Example 31. Products were isolated as either the free bases or hydrochloride salts. All $^1$H NMR are consistent with the structures shown.

Examples 75-80 were prepared from D8 and the appropriate alcohol using an analogous procedure to Example 31. Products were Isolated as either the free bases or hydrochloride salts. All $^1$H NMR are consistent with the structures shown.

Examples 81-84 and 163-181 were prepared from D14 and the appropriate alcohol using an analogous procedure to Example 31. Products were isolated as either the free bases or hydrochloride salts. All $^1$H NMR are consistent with the structures shown.

Examples 85-87 were prepared from D15 and the appropriate alcohol using an analogous procedure to Example 31. Products were isolated as either the free bases or hydrochloride salts. All $^1$H NMR are consistent with the structures shown.

Examples 144-149 were prepared from D29 and the appropriate alcohol using an analogous procedure to Example 31. Products were Isolated as either the free bases or hydrochloride salts. All $^1$H NMR are consistent with the structures shown.

Examples 150-160 were prepared from D30 and the appropriate alcohol using an analogous procedure to Example 31. Products were isolated as either the free bases or hydrochloride salts. All $^1$H NMR are consistent with the structures shown.

EXAMPLE 88

(4-Fluoro-benzyl)-[4-(8-methoxy-3-methyl-2,3,4,5-tetrahydro-1H-3-benzazepine-7-sulfonyl)-phenyl]-amine hydrochloride (E88)

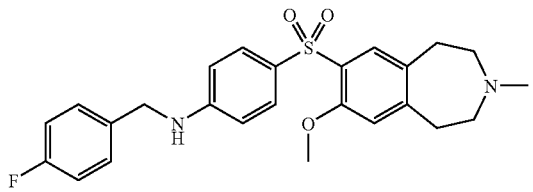

The aniline D10 (0.867 mmol, 300 mg) was dissolved in 1,2-dichloroethane (15 mL) and 4-fluorobenzaldehyde (7.6 eq., 6.6 mmol, 0.818 g) was added. The mixture was stirred at room temperature for 30 minutes and sodium triacetoxyborohydride (3.2 eq., 2.77 mmol, 0.588 g) was added and stirred for 14 hours. The reaction mixture was poured onto NaHCO$_3$ (saturated solution) (50 mL), vigorously stirred for 10 minutes and the organics were separated from the aqueous, dried over Na$_2$SO$_4$, filtered and the solvent was evaporated to afford 450 mg of crude product as a pale yellow solid. Chromatography on silica eluting with 0-10% MeOH—NH$_3$—DCM afforded 300 mg of the title compound E88 (76%), which was converted to the hydrochloride salt and isolated as a white solid. MH+ 455.

Examples 89-103 and 185 were prepared from the aniline D10 and the appropriate aldehyde using an analogous procedure to Example 88. Products were Isolated as either the free bases or hydrochloride salts. All $^1$H NMR are consistent with the structures shown.

EXAMPLE 104

[4-(8-Methoxy-3-methyl-2,3,4,5-tetrahydro-1H-3-benzazepine-7-sulfonyl)-phenyl]-phenyl-amine hydrochloride (E104)

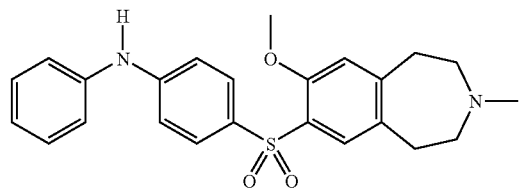

n-Butyllithium (1.0 mL, 1.6M in hexane, 1.6 mmol) was added to a solution of aniline (185 mg, 2.0 mmol) in tetrahydrofuran (2 mL) at −70° C. After the fluorosulfone D5 (180 mg, 0.5 mmol) was added and the solution stirred without cooling for 18 h. Water (20 mL) and ethyl acetate (20 mL) were added and the organic layer dried (MgSO$_4$) and evaporated. The resulting residue was chromatographed on silica gel eluting with 0 to 10% methanol in dichloromethane to give the title compound, isolated as the hydrochloride salt from diethyl ether (55 mg, 24%). MH+ 423.

Examples 105-106 and 197 were prepared from the fluorosulfone D5 and the appropriate aniline using an analogous procedure to Example 104, and optionally performing a subsequent reductive methylation using a procedure similar to Example 2 or by acylation (e.g. using formic acid) followed by reduction (e.g. using borane-THF).

Example 198 was prepared from the fluorosulfone D14 and the appropriate aniline using an analogous procedure to Example 104, and performing a subsequent reductive methylation using a procedure similar to Example 2 or by acylation (e.g. using formic acid) followed by reduction (e.g. using borane-THF).

Examples 199 and 201-203 were prepared from the fluorosulfone D29 and the appropriate aniline using an analogous procedure to Example 104, and performing a subsequent reductive methylation using a procedure similar to Example 2 or by acylation (e.g. using formic acid) followed by reduction (e.g. using borane-THF).

Example 200 was prepared from the fluorosulfone D30 and the appropriate aniline using an analogous procedure to Example 104, and performing a subsequent reductive methylation using a procedure similar to Example 2 or by acylation (e.g. using formic acid) followed by reduction (e.g. using borane-THF).

Products were isolated as either the free bases or hydrochloride salts. All $^1$H NMR are consistent with the structures shown.

EXAMPLE 107

7-[4(4-Chloro-phenoxymethyl)-benzenesulfonyl]-8-methoxy-3-methyl-2,3,4,5-tetrahydro-1H-3-benzazepine hydrochloride (E107)

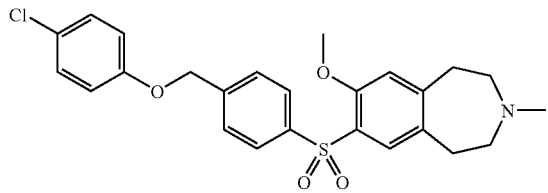

A solution of [4-(8-methoxy-3-methyl-2,3,4,5-tetrahydro-1-H-3-benzazepine-7-sulfonyl)-phenyl]-methanol D12 (0.12 g), 4-chlorophenol (0.042 g), triphenyl phosphine (0.087 g in tetrahydrofuran (5 mL) was treated with diisopropyl azodicarboxylate (0.066 g). The solution was stirred for 18 hour then the solvent was evaporated and the residue was purified by column chromatography on silica using 0-10% methanol (containing 0.5% aqueous ammonia)-dichloromethane to give the title compound E107, which was converted to the hydrochloride salt. $^1$H NMR: δ CDCl$_3$ 2.36 (3H, s), 2.55 (4H, m), 2.94 (4H, m), 3.73 (3H, s), 5.08 (2H, s) 6.64 (1H, s), 6.87 (2H, d), 7.22 (2H, d), 7.50 (2H, d) 7.84 (1H, s) 7.98 (2H, d). Mass Spectrum MH$^+$ 472

Examples 108 and 110 were prepared from D12 and the appropriate phenol using an analogous procedure to Example 107. Products were isolated as either the free bases or hydrochloride salts. All $^1$H NMR are consistent with the structures shown.

EXAMPLE 109

4-Chloro-phenyl)-[4-(8-methoxy-3-methyl-2,3,4,5-tetrahydro-1H-3-benzazepine-7-sulfonyl)-benzyl]-amine hydrochloride (109)

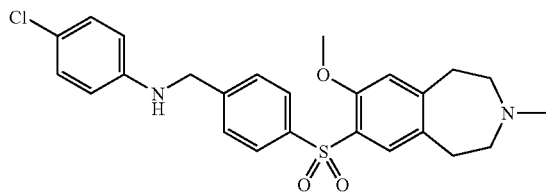

A solution of 4-(8-methoxy-3-methyl-2,3,4,5-tetrahydro-1-H-3-benzazepine-7-sulfonyl)-benzaldehyde D11 (0.12 g), 4-chloroaniline (0.050 g), in 1,2-dichloroethane (5 mL) was treated with sodium triacetoxyborohydride (0.25 g) The solution was stirred for 18 hour then dilute sodium hydroxide was added. The organic layer was separated, the solvent was evaporated and the residue was purified by column chromatography on silica using 0-10% methanol (containing 0.5% aqueous ammonia)-dichloromethane. The product was then treated with hydrogen chloride in ether to give the title compound E109 as a white solid. $^1$H NMR: δ DMSO 2.6 (3H, d), 3.0-3.3 (6H, m), 3.56 (2H, m), 3.58 (H, s) 4.35 (2H, s), 6.51 (2H, d), 7.04 (2H, d), 7.08 (1H, s) 7.53 (3H, m) 7.84 (3H, m), 10.95 (1H, br). Mass Spectrum MH$^+$ 471.

EXAMPLE 111

7-[4-4-Fluorobenzyl)benzenesulfonyl]—methoxy-3-methyl-2,3,4,5-tetrahydro-1H-3-benzazepine (E111)

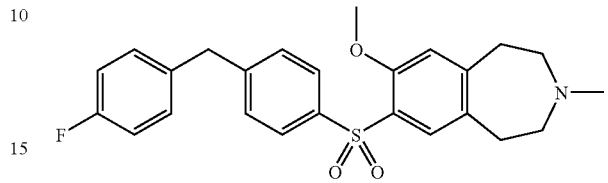

To a stirred solution of bromide D13 (98 mg, 0.239 mmol, 1.0 eq) in dry tetrahydrofuran (1 mL) was added 4-fluorobenzylzinc chloride (0.72 mL 0.5M solution in tetrahydrofuran, 0.358 mmol, 1.5 eq). The mixture was degassed with argon for 5 min. then Pd(PPh$_3$)$_4$ (14 mg, 0.012 mmol, 0.05 eq) added. The mixture was heated at 50° C. under argon for 2 h then allowed to cool to room temperature. The mixture was quenched with saturated aqueous NH$_4$Cl solution (1 mL), diluted with water (10 mL) then extracted with ethyl acetate (2×10 mL). The combined organic phase was washed sequentially with water (10 mL) and brine (10 mL) then dried over MgSO$_4$ and evaporated to dryness. Purification by Biotage chromatography, eluting with 1-5% MeOH—CH$_2$Cl$_2$ containing 0.5% NH$_3$ afforded the desired product as a solid, 63 mg (60%). MH$^+$ 440. $^1$H NMR δ (CDCl$_3$) 2.36 (3H, s), 2.55 (4H, m), 2.93 (4H, m), 3.73 (3H, s), 3.99 (2H, s), 6.63 (1H, s), 6.95 (2H, t), 7.08 (2H, m), 7.23 (2H, m), 7.87 (3H, m).

Example 213 was prepared using analogous procedures to Example 111 using the appropriate benzylzinc reagent and D13.

Example 212 was prepared using D14c following procedures similar to Descriptions D4 and D13 and Example E111.

Example 207 was prepared using analogous procedures to Example 111 using the appropriate benzylzinc reagent and D28.

EXAMPLE 115

7-[4-(3-Fluoro-benzyloxy)-benzenesulfonyl]-6-methoxy-1,2,3,4-tetrahydro-isoquinoline hydrochloride (E115)

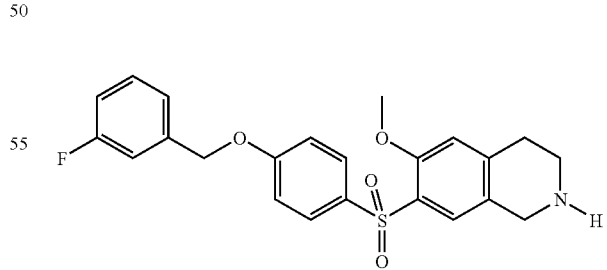

To a solution of D21 (174 mg, 0.33 mmol) in 1,4-dioxan (2 mL) was added hydrochloric acid (2 mL, 4M in 1,4-dioxan). The mixture was stirred overnight. Evaporation to dryness followed by trituration with ether yielded the title compound E115 as a solid (105 mg). MH$^+$ 428. $^1$H NMR δ (DMSO) 3.00-3.05 (2H, t), 3.31-3.37 (2H, t), 3.72 (3H, s), 4.29 (2H, s), 5.22 (2 h, s), 7.03 (1H, s), 7.12-7.33 (5H, m), 7.38-7.52 (1H, m), 7.75-7.82 (2H, d), 7.88 (1H, s), 9.30 (1H, br.s).

Examples 112-114 and Examples 116-127 were prepared from D20 and the appropriate alcohol using analogous procedures to Description D21 and Example 115. Products were isolated as either the free bases or hydrochloride salts. All $^1$H NMR are consistent with the structures shown.

EXAMPLE 131

5-Methoxy-2-methyl-6-[4-(3-trifluoromethyl-benzyloxy)-benzenesulfonyl]-2,3-dihydro-1H-isoindole hydrochloride (E131)

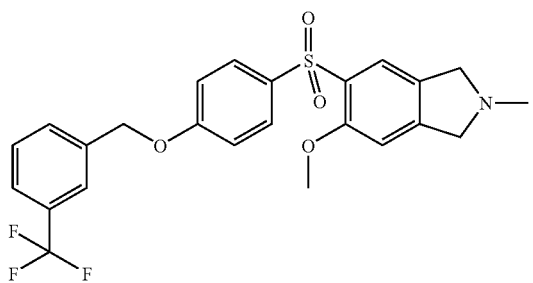

To a solution of 3-(trifluoromethyl) benzyl alcohol (109 mg, 0.62 mmol) in dry dimethylsulfoxide (2 mL) was added sodium hydride (17 mg, 0.43 mmol). The mixture was stirred at room temperature for 1 hour before the addition of D27 (100 mg, 0.31 mmol).

The resulting mixture was heated at 60° C. for 3 hours before allowing to cool and partitioning between ethyl acetate and water. The organic layer was removed and dried (MgSO$_4$), purification by SCX, followed by chromatography on silica eluting with dichloromethane up to 10% MeOH/NH$_3$/dichloromethane yielded the title compound as a solid (75 mg). The title compound was dissolved in dichloromethane and treated with 1M HCl in ether, the solvents were removed and the residue triturated with ether to yield the hydrochloride salt. MH$^+$ 478. $^1$H NMR δ (CDCl$_3$) 2.57 (3H, s), 3.73 (3H, s), 3.89 (4H, s), 5.14 (2H, s), 6.74 (1H, s), 6.95-7.05 (2H, d), 7.45-7.70 (4H, m), 7.85-7.96 (3H, m).

Examples 128-130 and Examples 132-143 were prepared from D27 and the appropriate alcohol using an analogous procedure to Example 131. Products were isolated as either the free bases or hydrochloride salts. All $^1$H NMR are consistent with the structures shown.

EXAMPLE 182

(2-Methoxy-benzyl)-[4-(8-methoxy-3-methyl-2,3,4,5-tetrahydro-1H-3-benzazepine-7-sulfonyl)-phenyl]-amine (E182)

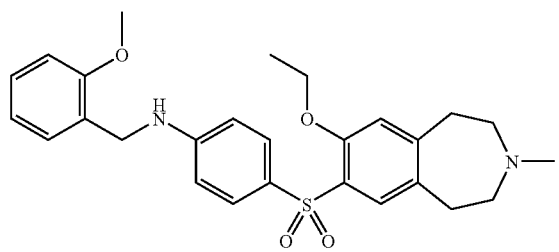

The title compound E182 was prepared from D14 in a manner similar to descriptions for D9, D10 and example E88 using 2-methoxybenzaldehyde for the final coupling. MH$^+$ 481

Examples E183 and 184 were prepared from the fluoro compound D14 using analogous procedures to Example E182.

Example E187 was prepared from E182 by performing a subsequent reductive methylation using a procedure similar to Example 2 or by acylation (e.g. using formic acid) followed by reduction (e.g. using borane-THF).

Examples E186-E196 were prepared from the appropriate 8-substituted benzazepine e.g. D10 and the appropriate benzaldehyde followed by reductive alkylation in a manner similar to E182 and E187.

EXAMPLE 204

7-[4-(4-Chloro-phenoxymethyl)-benzenesulfonyl]-8-ethoxy-3-methyl-2,3,4,5-tetrahydro-1H-3-benzazepine (E204)

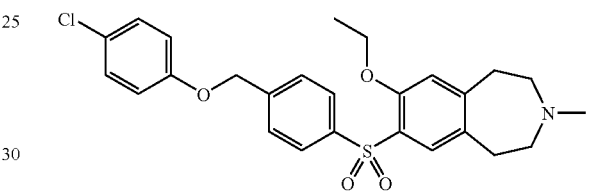

The title compound E204 was prepared from D14c in a manner similar to descriptions for D4, D11 and D12 and example E109 using 4-chlorophenol for the final coupling. MH$^+$ 487

Examples 110 and 205 were prepared using analogous procedures to Example 183 using the appropriate phenol. Products were isolated as either the free bases or hydrochloride salts. All $^1$H NMR are consistent with the structures shown.

EXAMPLE 206

[4-(8-Ethoxy-3-methyl-2,3,4,5-tetrahydro-1H-3-benzazepine-7-sulfonyl)-benzyl]-(2-methoxy-phenyl)-amine (E206)

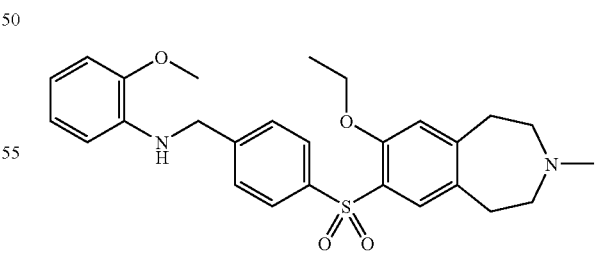

The title compound E206 was prepared from D14c in a manner similar to descriptions for D4 and D11 and example E109 using 2-methoxyaniline for the final coupling. MH$^+$ 481.

Examples 214 and 215 were prepared using analogous procedures to Example 206 using the appropriate aniline and were methylated by performing a subsequent reductive methylation using a similar procedure to Example 2 or by acylation (e.g. using formic acid) followed by reduction (e.g. using borane-THF). Products were isolated as either the free bases or hydrochloride salts. All $^1$H NMR are consistent with the structures shown.

EXAMPLE 208

{8-[4-4-(4-Fluoro-phenoxymethyl)-benzenesulfonyl]-3-methyl-2,3,4,5-tetrahydro-1H-3-benzazepin-7-yl}-dimethyl-amine (E208)

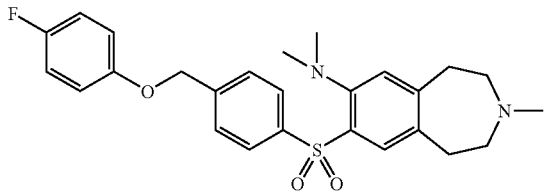

a) 4-(Dimethylamino-methyl-2,3,4,5-tetrahydro-1H-3-benzazepine-7-sulfonyl)-benzaldehyde

[8-(4-Bromo-benzenesulfonyl)$_3$-methyl-2,3,4,5-tetrahydro-1H-3-benzazepin-7-yl]-dimethyl-amine (D28) (1.4 g, 3.4 mmol) was cooled to −78° C. in tetrahydrofuran (20 ml) under an argon atmosphere. n-Butyllithium (1.6 ml, 2.5M) was added dropwise and the mixture stirred for 2 mins. Dimethylformamide (300 mg) was added and the mixture allowed to warm to room temperature then saturated ammonium chloride solution (50 ml) was added and the product extracted with ethyl acetate (2×50 ml). The organic layer was evaporated and chromatography on silica eluting with 0-20% methanol/ethyl acetate afforded the subtitled compound. MH$^+$ 373.

b) [4-(Dimethylamino-methyl-2,3,4,5-tetrahydro-1H-3-benzazepine-7-sulfonyl)-phenyl]-methanol 4-(8-Dimethylamino-3-methyl-2,3,4,5-tetrahydro-1H-3-benzazepine-7-sulfonyl)-benzaldehyde (880 mg) was dissolved in methanol (10 ml) and sodium borohydride (98 mg) was added and the mixture stirred for 20 min. Aqueous work up with dichloromethane (30 ml) and water (30 ml) and chromatography on silica eluting with 0-10% methanol/dichloromethane afforded the subtitled compound (423 mg) MH$^+$ 375.

c) {8-[4-(4Fluoro-phenoxymethyl)-benzenesulfonyl]-3-methyl-2,3,4,5-tetrahydro-1H-3-benzazepin-7-yl}-dimethyl-amine

[4-(Dimethylamino-methyl-2,3,4,5-tetrahydro-1H-3-benzazepine-7-sulfonyl)-phenyl]-methanol was converted to the title compound by using 4-fluorophenol and an analogous procedure to Example E107 to give the title compound e208. MH$^+$ 469.

Examples 209-211 were prepared using analogous procedures to Example 208 using the appropriate phenol. Products were isolated as either the free bases or hydrochloride salts. All $^1$H NMR are consistent with the structures shown.

Examples E216-E229 were prepared in the same manner as E109 and were optionally methylated by performing a subsequent reductive methylation using a similar procedure to Example 2 or by acylation (e.g. using formic acid) followed by reduction (e.g. using borane-THF). Products were isolated as either the free bases or hydrochloride salts. All $^1$H NMR are consistent with the structures shown.

EXAMPLE 230

6-Ethoxy-7-[4-(4-fluoro-benzyloxy)-benzenesulfonyl]-1,2,3,4-tetrahydro-isoquinoline hydrochloride (E230)

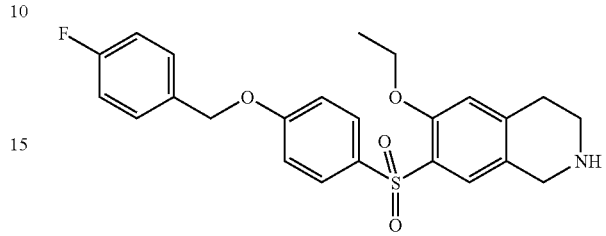

To a solution of 4-fluorobenzyl alcohol (169 mg, 1.34 mmol) in dry DMSO (1.2 mL) was added NaH (45 mg, 1.12 mmol). The mixture was stirred at room temperature for 30 minutes before the addition of D31 (150 mg, 0.45 mmol). The mixture was stirred at 60° C. for one hour. The mixture was quenched with water and extracted with ethyl acetate. The organic extracts were washed with brine, dried over sodium sulphate and evaporated to dryness. Purification by SCX followed by chromatography on silica, eluting with 1 to 10% MeOH/NH$_3$ in dichloromethane. Conversion of the free base to the hydrochloride salt was carried by dissolving the compound in dichloromethane and adding 1.05 equivalents HCl in ether. Evaporation to dryness gave the title compound as a pale coloured solid (52 mg). MH$^+$ 442. $^1$H NMR δ (CDCl$_3$) 1.25-1.37 (3H, t), 2.71-2.85 (2H, t), 3.07-3.17 (2H, t), 3.88-4.07 (4H, m), 5.06 (2H, s), 6.53 (1H, s), 6.95-7.15 (6H, m), 7.34-7.45 (2H, m), 7.77 (1H, s), 7.85-7.95 (2H, d).

Examples 231 and 232 were prepared using analogous procedures to Example 230 using the appropriate alcohol. Products were isolated as either the free bases or hydrochloride salts. All $^1$H NMR are consistent with the structures shown.

EXAMPLE 233

(3-Methoxy-benzyl)-[4-(6-methoxy-1,2,3,4-tetrahydro-isoquinoline-7-sulfonyl)-phenyl]-methyl-amine hydrochloride (E233)

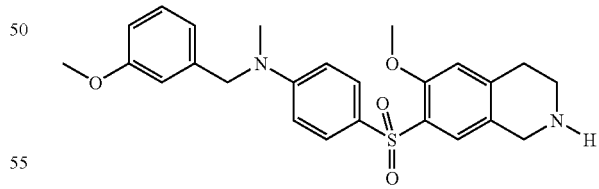

To a stirred solution of D32 (300 mg, 0.98 mmol) in THF (1.7 mL) at −78° C. was added dropwise n-butyllithium (2.5M, 0.4 mL, 1 mmol). The mixture was stirred for 30 minutes at —78° C. after which time D18 (112 mg, 0.33 mmol) in THF (0.5 mL) was added. The resulting mixture was stirred at −78° C. for 2 hours before quenching with acetic acid at −78° C. To the quenched mixture water was added and the pH adjusted to pH 7 using saturated sodium bicarbonate. Extraction with ethyl acetate followed by purification using chromatography on silica, eluting with 3 to 15% MeOH/NH$_3$ in dichloromethane. Conversion of the free base to the hydrochloride salt was carried by dissolving the compound in dichloromethane and adding 1.05 equivalents HCl in ether. Evaporation to dryness gave the title compound E233 as a pale coloured solid (70 mg). MH+ 453. $^1$H NMR δ (CDCl$_3$) 2.73-2.83 (2H, t), 3.06-3.17 (5H, m), 3.70-3.75 (6H, m), 4.00 (2H, s), 4.56 (2H, s), 6.55-6.83 (6H, m), 7.17-7.22 (1H, d), 7.73-7.81 (3H, m).

Examples 234-238 were prepared using analogous procedures to Example 233 using the appropriate aldehyde In D32. Products were isolated as either the free bases or hydrochloride salts. All $^1$H NMR are consistent with the structures shown.

Examples 239-242 were prepared using an analogous procedure to Example 233 using the appropriate arylbromide prepared according to D32. Products were isolated as either the free bases or hydrochloride salts. All $^1$H NMR are consistent with the structures shown.

EXAMPLE 243

7-[4(4-Chlorophenoxymethyl)benzenesulfonyl]-6-methoxy-1,2,3,4-tetrahydroisoquinoline hydrochloride salt (E243)

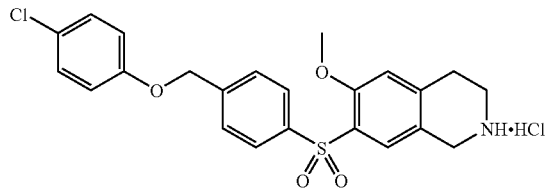

To a stirred solution of D36 in dry 1,4-dioxan (3 ml) under argon at room temperature was added 4M HCl in 1,4-dioxan (2 ml). The mixture was stirred at room temperature for 16 h then evaporated to dryness, affording the desired product E243 as a white solid (0.146 g, 100%). MH+ 444. $^1$H NMR: δ DMSO-d$^6$ 3.04 (2H, t), 3.34 (2H, m), 3.71 (3H, s), 4.30 (2H, s), 5.22 (2H, s), 7.03 (3H, m), 7.33 (2H, d), 7.64 (2H, d), 7.89 (3H, m), 9.49 (2H, br.s).

Examples 244-247 were prepared using an analogous procedure to Example 243 by using the appropriate phenols in Description D36. Products were isolated as either the free bases or hydrochloride salts. All $^1$H NMR are consistent with the structures shown.

EXAMPLE 248

3-Methyl-7-(4-(2-methoxybenzyl oxy)-phenylsulfonyl-9-phenyl-1,2,4,5-tetrahydro-3-benzazepine (E248)

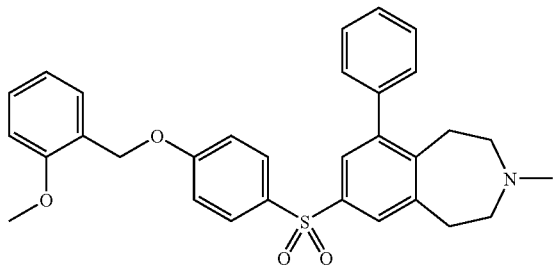

A solution of 2-methoxybenzyl alcohol (140 mg, 1 mmol) in DMSO (2 ml) was treated with sodium hydride (30 mg, 60% in oil, 0.75 mmol), and then 3-methyl-7-(4-fluorophenylsulfonyl)-9-phenyl-1,2,4,5tetrahydro-3-benzazepine (D37) (100 mg, 0.25 mmol) in more DMSO (1 ml). After heating for 1 h at 40° C., the solution was cooled and the product was isolated using an SCX column, and subsequent chromatography on silica, eluting with 0 to 10% methanol in dichloromethane containing 0.1M ammonia. The title compound E248) was collected as the hydrochloride salt from diethyl ether giving a white solid (65 mg). MH+ 514. $^1$H NMR δ (d$_6$-DMSO) 2.8 (3H, d), 3.0-3.6 (8H, m), 3.7 (3H, s), 3.9 (3H, s), 5.2 (2H, s), 6.9 (1H, t), 7.0 (1H, d), 7.2 (2H, d), 7.3-7.5 (7H, m), 7.6 (1H, s), 7.9 (1H, s), and 8.1 (2H, d).

Examples 249-265 were prepared using an analogous procedure to Example 248 by using the appropriate alcohols, phenols, amines and anilines and reacting with an appropriately substituted D37 analogue. Products were isolated as either the free bases or hydrochloride salts. All $^1$H NMR are consistent with the structures shown.

All of the compounds listed below in Table 1 relate to compounds of formula (IA), (IB), (ID), (IJ), (IK) and (IM) wherein Z represents —CH$_2$)$_r$O—:

TABLE 1

| Example | R$^1$ | R$^2$ | R$^3$ | R$^4$ | r | MH+ |
|---|---|---|---|---|---|---|
| 4 | H | H | Ph | H | 0 | 380 |
| 5 | Me | H | Ph | H | 0 | 394 |
| 6 | Me | H | Ph | H | 1 | 408 |
| 7 | H | H | 4-ClPh | H | 0 | 414 |
| 8 | Me | H | 4-ClPh | H | 0 | 428 |
| 9 | H | MeO | 4-ClPh | H | 0 | 444 |
| 10 | Me | H | Ph | H | 1 | 408 |
| 11 | H | H | 4-FPh | H | 0 | 398 |
| 12 | Me | H | 4-FPh | H | 0 | 412 |
| 13 | H | MeO | 4-FPh | H | 0 | 428 |
| 14 | Me | MeO | 4-FPh | H | 0 | 442 |
| 15 | Me | MeO | Ph | H | 1 | 438 |
| 16 | Me | MeO | 4-FPh | H | 1 | 456 |
| 17 | Me | MeO | 4-ClPh | H | 1 | 472 |

All of the compounds listed below in Table 2 relate to compounds of formulae (IA), (IC), (IE), (IJ), (IL), and (IM) and wherein Z represents —(CH$_2$)$_r$O—:

TABLE 2

| Example | R$^1$ | R$^2$ | R$^3$ | R$^4$ | r | MH+ |
|---|---|---|---|---|---|---|
| 18 | H | H | Ph | H | 0 | 380 |
| 19 | Me | H | Ph | H | 0 | 394 |
| 20 | H | MeO | Ph | H | 0 | 410 |
| 21 | Me | MeO | Ph | H | 0 | 424 |

TABLE 2-continued

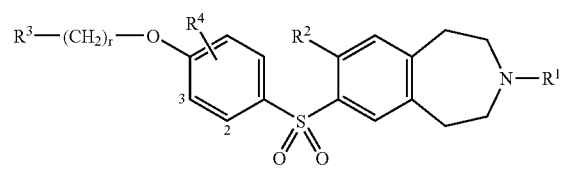

| Example | R¹ | R² | R³ | R⁴ | r | MH⁺ |
|---|---|---|---|---|---|---|
| 22 | H | H | Ph | H | 1 | 394 |
| 23 | Me | H | Ph | H | 1 | 408 |
| 24 | H | MeO | 4-ClPh | H | 0 | 444 |
| 25 | Me | MeO | 4-ClPh | H | 0 | 458 |
| 26 | H | MeO | 4-FPh | H | 0 | 437 |
| 27 | Me | MeO | 4-FPh | H | 0 | 442 |
| 28 | H | MeO | Ph | H | 1 | 424 |
| 29 | Me | MeO | Ph | H | 1 | 438 |
| 30 | Me | MeO | 4-FPh | H | 1 | 456 |
| 31 | Me | MeO | 4-ClPh | H | 1 | 472 |
| 32 | Me | MeO | 4-MePh | H | 1 | 452 |
| 33 | Me | MeO | 4-CF3Ph | H | 1 | 522 |
| 34 | Me | MeO | 4-BrPh | H | 1 | 517 |
| 35 | Me | MeO | 4-iPrPh | H | 1 | 480 |
| 36 | Me | MeO | 3-CF3Ph | H | 1 | 506 |
| 37 | Me | MeO | 2,4-diClPh | H | 1 | 507 |
| 38 | Me | MeO | 3,4-diClPh | H | 1 | 507 |
| 39 | Me | MeO | 2-Cl-4-FPh | H | 1 | 490 |
| 40 | Me | MeO | 2,6-diClPh | H | 1 | 507 |
| 41 | Me | MeO | 2-MeOPh | H | 1 | 468 |
| 42 | Me | MeO | 4-MeOPh | H | 1 | 468 |
| 43 | Me | MeO | 3,4-diFPh | H | 1 | 474 |
| 44 | Me | MeO | 2,4-diFPh | H | 1 | 474 |
| 45 | Me | MeO | 2,3-diFPh | H | 1 | 474 |
| 46 | Me | MeO | 3-FPh | H | 1 | 456 |
| 47 | Me | MeO | 4-CF3Ph | H | 1 | 506 |
| 48 | Me | MeO | 4-FPh | 2-Me | 1 | 470 |
| 49 | Me | MeO | 4-FPh | 3-Me | 1 | 470 |
| 50 | Me | MeO | 4-ClPh | 3-Me | 1 | 486 |
| 51 | Me | MeO | 4-ClPh | 3-F | 1 | 490 |
| 52 | Me | MeO | 6-methyl-2-pyridyl | H | 1 | 453 |
| 53 | Me | MeO | 4-pyridyl | H | 1 | 439 |
| 54 | Me | MeO | 2-pyridyl | H | 1 | 439 |
| 55 | Me | MeO | 3-pyridyl | H | 1 | 439 |
| 56 | Me | MeO | 5-methyl-isoxazol-3-yl | H | 1 | 443 |
| 57 | Me | MeO | 2-thienyl | H | 1 | 444 |
| 58 | Me | MeO | 5-methyl-2-thienyl | H | 1 | 458 |
| 59 | Me | MeO | 3-methyl-2-thienyl | H | 1 | 458 |
| 60 | Me | MeO | 5-chloro-2-thienyl | H | 1 | 479 |
| 61 | Me | MeO | 2-furyl | H | 1 | 428 |
| 62 | Me | MeO | 4,5-dimethyl-2-furyl | H | 1 | 456 |
| 63 | Me | MeO | 5-methyl-2-trifluoromethyl-3-furyl | H | 1 | 510 |
| 64 | Me | MeO | 5-ethyl-2-furyl | H | 1 | 456 |
| 65 | Me | MeO | 2-thiazolyl | H | 1 | 445 |
| 66 | Me | MeO | 2-benzofuryl | H | 1 | 478 |
| 67 | Me | MeO | 5-dihydro-1-benzofuryl | H | 1 | 480 |
| 68 | Me | MeO | 3-benzothienyl | H | 1 | 494 |
| 69 | Me | MeO | 2-benzothienyl | H | 1 | 494 |
| 70 | Me | MeO | 5-chloro-3-benzothienyl | H | 1 | 529 |
| 71 | Me | MeO | 3-methyl-2-benzothienyl | H | 1 | 508 |
| 72 | Me | MeO | 3,4-methylenedioxyphenyl | H | 1 | 482 |
| 73 | Me | MeO | 2,3-dihydro-benzo[1,4]dioxin-6-yl | H | 1 | 496 |

TABLE 2-continued

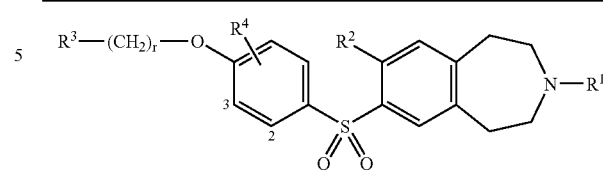

| Example | R¹ | R² | R³ | R⁴ | r | MH⁺ |
|---|---|---|---|---|---|---|
| 74 | Me | MeO | 2,3-dihydro-benzo[1,4]dioxin-2-yl | H | 1 | 496 |
| 75 | Me | Me | 3-CF3Ph | H | 1 | 490 |
| 76 | Me | Me | 3,4-diFPh | H | 1 | 458 |
| 77 | Me | Me | 3-FPh | H | 1 | 440 |
| 78 | Me | Me | 4-FPh | H | 1 | 440 |
| 79 | Me | Me | 4-FPh | H | 0 | 426 |
| 80 | Me | Me | 4-ClPh | H | 1 | 456 |
| 81 | Me | EtO | 3-FPh | H | 1 | 470 |
| 82 | Me | EtO | 4-FPh | H | 0 | 456 |
| 83 | Me | EtO | 4-FPh | H | 1 | 470 |
| 84 | Me | EtO | 4-ClPh | H | 1 | 487 |
| 85 | Me | EtS | 4-FPh | H | 0 | 472 |
| 86 | Me | EtS | 3-FPh | H | 1 | 486 |
| 87 | Me | EtS | 4-ClPh | H | 1 | 503 |
| 144 | Me | iPrO | 4-ClPh | H | 1 | 501 |
| 145 | Me | iPrO | 4-FPh | H | 0 | 470 |
| 146 | Me | iPrO | 4-ClPh | H | 0 | 487 |
| 147 | Me | iPrO | 4-MePh | H | 0 | 466 |
| 148 | Me | iPrO | 3,4-FPh | H | 0 | 488 |
| 149 | Me | iPrO | 2,4-FPh | H | 0 | 488 |
| 150 | Me | Me₂N | 4-ClPh | H | 1 | 486 |
| 151 | Me | Me₂N | 4-FPh | H | 0 | 455 |
| 152 | Me | Me₂N | 4-MePh | H | 0 | 451 |
| 153 | Me | Me₂N | 4-ClPh | H | 0 | 472 |
| 154 | Me | Me₂N | 3,4-FPh | H | 0 | 473 |
| 155 | Me | Me₂N | 2,4-FPh | H | 0 | 473 |
| 156 | Me | Me₂N | 4-ClPh | H | 1 | 469 |
| 157 | Me | Me₂N | 4-CF3Ph | H | 1 | 519 |
| 158 | Me | Me₂N | 3,4-FPh | H | 1 | 487 |
| 159 | Me | Me₂N | 2,4-FPh | H | 1 | 487 |
| 160 | Me | Me₂N | 2,3-FPh | H | 1 | 487 |
| 161 | Me | MeO | 4-FPh | 3-Cl | 0 | 476 |
| 162 | iPr | MeO | 4-ClPh | H | 1 | 501 |
| 163 | Me | EtO | 3,4-FPh | H | 0 | 474 |
| 164 | Me | EtO | 2,4-FPh | H | 0 | 474 |
| 165 | Me | EtO | 4-ClPh | H | 0 | 473 |
| 166 | Me | EtO | 4-FPh | 3-Cl | 0 | 491 |
| 167 | Me | EtO | 4-MePh | H | 0 | 452 |
| 168 | Me | EtO | 2,5-FPh | H | 0 | 474 |
| 169 | Me | EtO | 2,4-ClPh | H | 0 | 507 |
| 170 | Me | EtO | 2-Cl, 4-MeOPh | H | 0 | 503 |
| 171 | Me | EtO | 2-Cl, 4-FPh | H | 0 | 491 |
| 172 | Me | EtO | 3-Cl, 4-FPh | H | 0 | 491 |
| 173 | Me | EtO | 4-Cl, 3-FPh | H | 0 | 491 |
| 174 | Me | EtO | 4-F, 2-MeOPh | H | 0 | 486 |
| 175 | Me | EtO | 4-F, 2-MePh | H | 0 | 470 |
| 176 | Me | EtO | 4-F, 3-MePh | H | 0 | 470 |
| 177 | Me | EtO | 4-Cl, 2-MePh | H | 0 | 487 |
| 178 | Me | EtO | 4-Cl, 3-MePh | H | 0 | 487 |
| 179 | Me | EtO | 3,4-ClPh | H | 0 | 507 |
| 180 | Me | EtO | 3-CF3, 4-ClPh | H | 0 | 541 |
| 181 | Me | EtO | 2-F, 4-ClPh | H | 0 | 491 |

All of the compounds listed below in Table 3 relate to compounds of formulae (IA), (IC), (IE), (IJ), and (IL) wherein Z represents —(CH₂)$_r$NR⁷:

TABLE 3

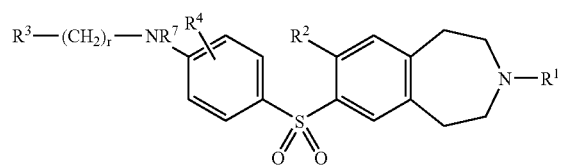

| Example | R¹ | R² | R³ | R⁴ | r | NR⁷ | MH⁺ |
|---|---|---|---|---|---|---|---|
| 88 | Me | MeO | 4-FPh | H | 1 | NH | 455 |
| 89 | Me | MeO | 4-MeOPh | H | 1 | NH | 467 |
| 90 | Me | MeO | 3-CF₃Ph | H | 1 | NH | 505 |
| 91 | Me | MeO | 2-MeOPh | H | 1 | NH | 467 |
| 92 | Me | MeO | 3-FPh | H | 1 | NH | 455 |
| 93 | Me | MeO | 4-ClPh | H | 1 | NH | 471 |
| 94 | Me | MeO | 3,4-diFPh | H | 1 | NH | 473 |
| 95 | Me | MeO | 4-CF₃Ph | H | 1 | NH | 505 |
| 96 | Me | MeO | 4-MeOCH₂Ph | H | 1 | NH | 481 |
| 97 | Me | MeO | 4-MeCOPh | H | 1 | NH | 479 |
| 98 | Me | MeO | 4-FPh | H | 1 | NMe | 469 |
| 99 | Me | MeO | 5-Me-2-thienyl | H | 1 | NH | 457 |
| 100 | Me | MeO | 5-Cl-2-thienyl | H | 1 | NH | 477 |
| 101 | Me | MeO | 3-benzothienyl | H | 1 | NH | 493 |
| 102 | Me | MeO | 2-benzofuranyl | H | 1 | NH | 477 |
| 103 | Me | MeO | 2-benzothienyl | H | 1 | NH | 493 |
| 104 | Me | MeO | Ph | H | 0 | NH | 423 |
| 105 | Me | MeO | Ph | H | 0 | NMe | 437 |
| 106 | Me | MeO | 4-FPh | H | 0 | NH | 441 |
| 182 | Me | EtO | 4-FPh | H | 1 | NH | 469 |
| 183 | Me | EtO | 2-MeOPh | H | 1 | NH | 481 |
| 184 | Me | EtO | 4-MeOPh | H | 1 | NH | 481 |
| 185 | Me | MeO | 4-CNPh | H | 1 | NH | 462 |
| 186 | Me | MeO | 4-ClPh | H | 1 | NMe | 485 |
| 187 | Me | EtO | 4-FPh | H | 1 | NMe | 483 |
| 188 | Me | i-PrO | 4-FPh | H | 1 | NMe | 497 |
| 189 | Me | Me₂N | 4-FPh | H | 1 | NMe | 482 |
| 190 | Me | Me₂N | 4-MeOPh | H | 1 | NMe | 494 |
| 191 | Me | Me₂N | 4-ClPh | H | 1 | NMe | 498 |
| 192 | Me | MeO | 3,4-diCl | H | 1 | NMe | 520 |
| 193 | Me | MeO | 4-CF₃Ph | H | 1 | NMe | 519 |
| 194 | Me | MeO | 3-Cl-4-FPh | H | 1 | NMe | 503 |
| 195 | Me | MeO | 3-CF₃Ph | H | 1 | NMe | 519 |
| 196 | Me | MeO | 4-CF₃OPh | H | 1 | NMe | 534 |
| 197 | Me | MeO | 4-ClPh | H | 0 | NH | 457 |
| 198 | Me | EtO | 4-FPh | H | 0 | NMe | 469 |
| 199 | Me | i-PrO | 4-FPh | H | 0 | NMe | 483 |
| 200 | Me | Me₂N | 4-FPh | H | 0 | NMe | 468 |
| 201 | Me | i-PrO | 4-ClPh | H | 0 | NMe | 499 |
| 202 | Me | i-PrO | 3-ClPh | H | 0 | NMe | 499 |
| 203 | Me | i-PrO | 3,4-diFPh | H | 0 | NMe | 501 |

All of the compounds listed below in Table 4 relate to compounds of formulae (IA), (IC), (IE), (IJ), and (IL) wherein Z represents —X(CH₂)ᵣ—;

TABLE 4

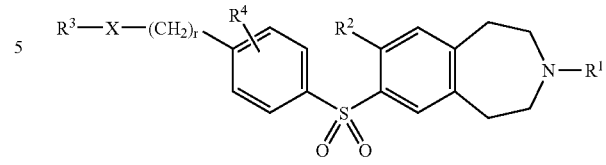

| Example | R¹ | R² | R³ | R⁴ | r | X | MH⁺ |
|---|---|---|---|---|---|---|---|
| 107 | Me | MeO | 4-ClPh | H | 1 | O | 472 |
| 108 | Me | MeO | 4-FPh | H | 1 | O | 456 |
| 109 | Me | MeO | 4-ClPh | H | 1 | NH | 471 |
| 110 | Me | EtO | 4-FPh | H | 1 | O | 470 |
| 111 | Me | MeO | 4-FPh | H | 0 | CH₂ | 440 |
| 204 | Me | EtO | 4-ClPh | H | 1 | O | 487 |
| 205 | Me | EtO | 4-CF₃Ph | H | 1 | O | 520 |
| 206 | Me | EtO | 2-MeOPh | H | 1 | NH | 481 |
| 207 | Me | Me₂N | 4-FPh | H | 0 | CH₂ | 453 |
| 208 | Me | Me₂N | 4-FPh | H | 1 | O | 469 |
| 209 | Me | Me₂N | 4-ClPh | H | 1 | O | 486 |
| 210 | Me | Me₂N | 4-CF₃Ph | H | 1 | O | 519 |
| 211 | Me | Me₂N | 2-Cl, 4-FPh | H | 1 | O | 504 |
| 212 | Me | EtO | 4-FPh | H | 0 | CH₂ | 454 |
| 213 | Me | MeO | 3-FPh | H | 0 | CH₂ | 440 |
| 214 | Me | EtO | 4-FPh | H | 1 | NMe | 483 |
| 215 | Me | EtO | 4-ClPh | H | 1 | NMe | 500 |
| 216 | Me | MeO | 4-FPh | H | 1 | NH | 455 |
| 217 | Me | MeO | 4-ClPh | H | 1 | NMe | 485 |
| 218 | Me | MeO | 3-ClPh | H | 1 | NH | 471 |
| 219 | Me | MeO | 2-MeOPh | H | 1 | NH | 467 |
| 220 | Me | MeO | 4-MeOPh | H | 1 | NH | 467 |
| 221 | Me | MeO | 4-MeOPh | H | 1 | NMe | 481 |
| 222 | Me | MeO | 4-i-PrPh | H | 1 | NH | 479 |
| 223 | Me | MeO | 2-Me-4-ClPh | H | 1 | NH | 485 |
| 224 | Me | MeO | 4-CF₃OPh | H | 1 | NH | 521 |
| 225 | Me | MeO | 2,4-diClPh | H | 1 | NH | 506 |
| 226 | Me | MeO | 3,4-diClPh | H | 1 | NH | 506 |
| 227 | Me | MeO | 2-Cl-4-FPh | H | 1 | NH | 489 |
| 228 | Me | MeO | 4-FPh | H | 1 | NMe | 469 |
| 229 | Me | MeO | 3-ClPh | H | 1 | NMe | 485 |

All of the compounds listed below in Table 5 relate to compounds of formulae (IA), (IC), (IE), (IG), and (IM) wherein Z represents —(CH₂)ᵣO—;

TABLE 5

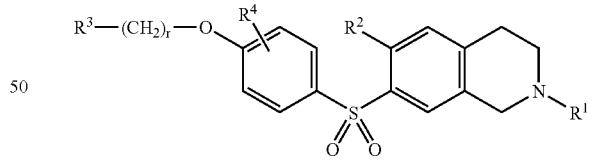

| Example | R¹ | R² | R³ | R⁴ | r | MH⁺ |
|---|---|---|---|---|---|---|
| 112 | H | MeO | 3-ClPh | H | 1 | 444 |
| 113 | H | MeO | 4-FPh | H | 0 | 415 |
| 114 | H | MeO | 4-FPh | H | 1 | 428 |
| 115 | H | MeO | 3-FPh | H | 1 | 428 |
| 116 | H | MeO | 3,4-diFPh | H | 1 | 446 |
| 117 | H | MeO | 3-CF₃Ph | H | 1 | 478 |
| 118 | H | MeO | 4-CF₃Ph | H | 1 | 477 |
| 119 | H | MeO | 2-benzofuryl | H | 1 | 450 |
| 120 | H | MeO | 5-Cl-2-thienyl | H | 1 | 450 |
| 121 | H | MeO | 3-Me₂NPh | H | 1 | 453 |
| 122 | H | MeO | 2-benzothienyl | H | 1 | 466 |
| 123 | H | MeO | 3-MeOPh | H | 1 | 440 |
| 124 | H | MeO | 3-CNPh | H | 1 | 435 |
| 125 | H | MeO | 3,4-diMeOPh | H | 1 | 470 |

TABLE 5-continued

| Example | R¹ | R² | R³ | R⁴ | r | MH⁺ |
|---|---|---|---|---|---|---|
| 126 | H | MeO | 3,4,5-triMeOPh | H | 1 | 500 |
| 127 | H | MeO | 2-naphthyl | H | 1 | 460 |
| 231 | H | OEt | 3-FPh | H | 1 | 442 |
| 232 | H | OEt | 4-MeOPh | H | 1 | 454 |

All of the compounds listed below in Table 6 relate to compounds of formulae (IA), (IC), (IE), (IF) and (IM) wherein Z represents —(CH$_2$)$_r$O—;

TABLE 6

| Example | R¹ | R² | R³ | R⁴ | r | MH⁺ |
|---|---|---|---|---|---|---|
| 128 | Me | MeO | 4-ClPh | H | 1 | 444 |
| 129 | Me | MeO | 4-FPh | H | 0 | 414 |
| 130 | Me | MeO | 3,4-diFPh | H | 1 | 446 |
| 131 | Me | MeO | 3-CF₃Ph | H | 1 | 478 |
| 132 | Me | MeO | 4-FPh | H | 1 | 428 |
| 133 | Me | H | 4-ClPh | H | 1 | 415 |
| 134 | Me | H | 3-CF₃Ph | H | 1 | 448 |
| 135 | Me | MeO | 2-CF₃Ph | H | 1 | 478 |
| 136 | Me | MeO | 3-MeOPh | H | 1 | 440 |
| 137 | Me | MeO | 3-ClPh | H | 1 | 444 |
| 138 | Me | MeO | 4-CF₃Ph | H | 1 | 478 |
| 139 | Me | MeO | 3-Me₂NPh | H | 1 | 453 |
| 140 | Me | MeO | 5-Cl-2-thienyl | H | 1 | 450 |
| 141 | Me | MeO | 1-benzofuran-2 | H | 1 | 450 |
| 142 | Me | MeO | 3-CNPh | H | 1 | 435 |
| 143 | Me | MeO | 2-naphthyl | H | 1 | 460 |

All of the compounds listed below in Table 7 relate to compounds of formulae (IA), (IC), (IE) and (IG) wherein Z represents —(CH$_2$)$_r$NR$^7$:

TABLE 7

| Example | R¹ | R² | R³ | R⁴ | r | NR⁷ | MH⁺ |
|---|---|---|---|---|---|---|---|
| 234 | H | MeO | 3-FPh | H | 1 | NMe | 441 |
| 235 | H | MeO | 4-ClPh | H | 1 | NMe | 457 |
| 236 | H | MeO | 4-MeOPh | H | 1 | NMe | 453 |
| 237 | H | MeO | 5-chloro-2-thienyl | H | 1 | NMe | 463 |
| 238 | H | MeO | 4-CF₃Ph | H | 1 | NMe | 491 |

All of the compounds listed below in Table 8 relate to compounds of formulae (IA), (IC), (IE) and (IG) wherein Z represents —X(CH$_2$)$_r$—:

TABLE 8

| Example | R¹ | R² | R³ | R⁴ | r | X | MH⁺ |
|---|---|---|---|---|---|---|---|
| 239 | H | MeO | 4-FPh | H | 1 | NMe | 441 |
| 240 | H | MeO | 4-ClPh | H | 1 | NMe | 457 |
| 241 | H | MeO | 3-ClPh | H | 1 | NMe | 457 |
| 242 | H | MeO | 4-MeOPh | H | 1 | NMe | 453 |
| 244 | H | MeO | 4-FPh | H | 1 | O | 428 |
| 245 | H | MeO | 4-CF₃Ph | H | 1 | O | 478 |
| 246 | H | MeO | 3-FPh | H | 1 | O | 428 |
| 247 | H | MeO | 3-Me₂NPh | H | 1 | O | 453 |

All of the compounds listed below in Table 9 relate to compounds of formulae (IC), (IJ) and (IN);

TABLE 9

| Example | R¹ | R² | R³ | R⁴ | Z | MH⁺ |
|---|---|---|---|---|---|---|
| 249 | Me | Ph | 4-ClPh | H | CH₂O | 518 |
| 250 | Me | Ph | 3-MeOPh | H | CH₂O | 514 |
| 251 | Me | Ph | 2-naphthyl | H | CH₂O | 534 |
| 252 | Me | 4-MeOPh | 3-MeOPh | H | CH₂O | 544 |
| 253 | Me | Ph | 4-MeOPh | H | CH₂O | 514 |
| 254 | Me | 4-NH₂COPh | 3-MeOPh | H | CH₂O | 557 |
| 255 | Me | Ph | 3-pyridyl | H | CH₂O | 485 |
| 256 | Me | 4-FPh | 3-MeOPh | H | CH₂O | 532 |
| 257 | Me | 3-thienyl | 3-MeOPh | H | CH₂O | 520 |
| 258 | Me | 3-AcNHPh | 3-MeOPh | H | CH₂O | 571 |
| 259 | Me | 4-FPh | 3-ClPh | H | CH₂O | 537 |
| 260 | Me | 4-FPh | 4-CF₃Ph | H | CH₂O | 570 |
| 261 | Me | 4-FPh | 4-MeOPh | H | CH₂O | 532 |
| 262 | Me | Ph | 4-FPh | H | O | 488 |
| 263 | Me | 4-FPh | 4-FPh | H | NMe | 519 |
| 264 | Me | Ph | 4-FPh | H | NH | 487 |
| 265 | Me | 4-FPh | 4-FPh | H | CH₂NMe | 533 |

All publications, including but not limited to patents and patent applications, cited in this specification are herein incorporated by reference as if each individual publication were specifically and individually indicated to be incorporated by reference herein as though fully set forth.

The invention claimed is:

1. A compound which is 7-[4-(4-Chloro-benzyloxy)-benzenesulfonyl]-8-methoxy-3-methyl-2,3,4,5-tetrahydro-1H-3-benzazepine, or a pharmaceutically acceptable salt thereof.

2. A compound which is 7-[4-(4-Chloro-benzyloxy)-benzenesulfonyl]-8-methoxy-3-methyl-2,3,4,5-tetrahydro-1H-3-benzazepine, as the free base.

3. A compound which is 7-[4-(4-Chloro-benzyloxy)-benzenesulfonyl]-8-methoxy-3-methyl-2,3,4,5-tetrahydro-1H-3-benzazepine hydrochloride.

4. A pharmaceutically acceptable composition comprising 7-[4-(4-Chloro-benzyloxy)-benzenesulfonyl]-8-methoxy-3-methyl-2,3,4,5-tetrahydro-1H-3-benzazepine, or a pharmaceutically acceptable salt thereof, and a pharmaceutically acceptable excipient.

5. A pharmaceutically acceptable composition comprising 7-[4-(4-Chloro-benzyloxy)-benzenesulfonyl]-8-methoxy-3-methyl-2,3,4,5-tetrahydro-1H-3-benzazepine hydrochloride, and a pharmnaceutically acceptable excipient.

6. A method for treating schizophrenia comprising administering a therapeutically effective amount of the compound 7-[4-(4-Chloro-benzyloxy)-benzenesulfonyl]-8-methoxy-3-methyl-2,3,4,5-tetrahydro-1H-3-benzazepine, or a pharmaceutically acceptable salt thereof, neat or as a pharmnaceutically acceptable composition to a human in need thereof.

7. A method for treating schizophrenia comprising administering a therapeutically effective amount of the compound 7-[4-(4-Chloro-benzyloxy)-benzenesulfonyl]-8-methoxy-3-methyl-2,3,4,5-tetrahydro-1H-3-benzazepine hydrochloride.

\* \* \* \* \*